United States Patent [19]

Cheng et al.

[11] Patent Number: 5,985,605
[45] Date of Patent: Nov. 16, 1999

[54] DNA SEQUENCES ENCODING PHYTASES OF RUMINAL MICROORGANISMS

[75] Inventors: Kuo Joan Cheng; Leonard Brent Selinger; Lindsey Jay Yanke, all of Lethbridge, Canada; Hee Dong Bae, Seoul, Rep. of Korea; Luming Zhou, Salt Lake City, Utah; Cecil Wallace Forsberg, Guelph, Canada

[73] Assignee: Her Majesty the Queen in right of Canada, as represented by the Dept. of Agriculture & Agri-Food Canada, Lethbridge, Canada

[21] Appl. No.: 08/862,531

[22] Filed: May 23, 1997

Related U.S. Application Data

[63] Continuation-in-part of application No. 08/744,779, Nov. 6, 1996
[60] Provisional application No. 60/019,735, Jun. 14, 1996.
[51] Int. Cl.$^6$ ............ C12N 15/31; C12N 15/55; C12N 9/14; C12N 1/15; C12N 1/21; C12N 5/10; A01H 5/00
[52] U.S. Cl. ............ 435/69.1; 536/23.7; 536/23.2; 435/172.3; 435/196; 435/252.3; 435/252.31; 435/252.33; 435/254.23; 435/254.11; 435/419; 435/325; 800/205
[58] Field of Search ............ 536/23.7, 23.2; 435/69.1, 172.3, 196, 252.3, 252.31, 252.33, 254.23, 254.11, 419, 325; 800/205

[56] References Cited

U.S. PATENT DOCUMENTS

| | | |
|---|---|---|
| 3,297,548 | 1/1967 | Ware et al. ............ 195/66 |
| 5,436,156 | 7/1995 | Van Gorcom et al. ............ 435/252.3 |

FOREIGN PATENT DOCUMENTS

| | | | |
|---|---|---|---|
| 0420358A1 | 4/1991 | European Pat. Off. . | |
| 0449375A2 | 10/1991 | European Pat. Off. . | |
| 684313 | 11/1995 | European Pat. Off. | C12N 15/55 |
| 699762 | 3/1996 | European Pat. Off. | C12N 15/55 |
| WO 93/16175 | 8/1993 | WIPO . | |
| WO 94/03072 | 2/1994 | WIPO . | |

OTHER PUBLICATIONS

Punj, M.L. et al. "Utilization of Phytin Phosphorus by Rumen Microorganisms". The Indian Veterinary Journal, vol. 46, No. 10, 1969 pp. 881–886, at p. 885.

Ausubel, F.A. Brent, R., Kingston, R.E., Moore, D.D., Sneidman, J.G. Smith, J.A. and Struhl, K. (eds.) 1990. Current Protocols in Molecular Biology. Green Publishing and Wiley–Interscience, New York.

Jurgen Brosius, Mary Erfle and Storella, John 1985. Spacing of the –10 and –35 regions in the tac Promoter. J. Biol. Chem. 260:3539–3541.

Bryant, M.P. and Burkey, L.A. 1953. Cultural Methods and Some Characteristics of Some of the Numerous Groups of Bacteria in the Bovine Rumen. J. Dairy Sci. 36:205–217.

Cheng, E.W., Hall, Glen andBurroughs, Wise 1955. A Method for the Study of Cellulose Digestion by Washed Suspensions of Rumen Microorganisms. J. Dairy Sci. 38:1255–1230.

Cheng, K.–J. and Costerton, J.W. 1973. Localization of Alkaline Phosphatase in Three Gram–Negative Rumen Bacteria. J. Bacteriol. 116:424–440.

Ellis, S.B., Brust, P.F., Koutz, P.J., Waters, A.F., Harpold, M.M. and Gingeras, T.R. 1985. Isolation of Alcohol Oxidase and Two Other Methanol Regulated Genes from the Yeast *Pichia pastoris*. Mol. Cell. Biol. 5:1111–1121.

Fiske, Cyrus H. and Subbarow, Yellapragada 1925. The Colorimetric Determination of phosphorus. J. Biol. Chem. 66:376–400.

Gelvin, Stanton B., Schilperoort, R.A. and Verma, D.P.S. (eds.) 1993. Plant Molecular Biology Manual. Kluwer Academic Publishers, Boston, MA.

Graf, Enest (ed.) 1986. Phytic Acid, Chemistry and Applications. Pilatus Press. Minneapolis MN. 344 pp.

Howson, S.J. and Davs, R.P. 1983. Production of Phytase–hydrolysing Enzyme by Some Fungi. Enzyme Microb. Technol. 5:377–382.

Hu, Y.J., Smith, D.C., Cheng, K.–J. and Forsberg, Cecil W. 1991. Cloning of a Xylanase Gene from *Fibrobacter succinogenes* 135 and Its Expression in *Esherichia coli*. Can.J. Microbiol. 37:554–561.

Hungate, R.E. 1950. The Anaerobin Mesophilic Cellulolytic Bacteria. Bacteriol. Rev. 14:1–49.

Laemmli, U.K. 1970. Cleavage of the Structural Proteins During Assembly of the Head of Bacteriophage T4. Nature 227:680–685.

Priefer, U., Simon, R. And Puhler, A. 1984. Cloning with Cosmids. In: Puhler, A. And Timmis, K.N. (eds). Advanced Molecular Genetics. Springer–Verlag, New York 190–201 pp.

Raun, Arthur, Cheng, E. And Buroughs, W. 1956. Phytate phosphorus Hydrolysis and Availability to Rumen Microorganisms. Agric. Food Chem. 4:869–871.

Sambrook, J., Fritsch, E.F. and Maniatis, T. 1989. Molecular Cloning. A Laboratory Manual. 2nd edn. Cold Spring Harbor Laboratory Press. Cold Spring Harbor, NY.

(List continued on next page.)

*Primary Examiner*—Mary E. Mosher
*Attorney, Agent, or Firm*—Greenlee, Winner & Sullivan, P.C.

[57] ABSTRACT

Novel phytases derived from ruminal microorganisms are provided. The phytases are capable of catalyzing the release of inorganic phosphorus from phytic acid. Preferred sources of phytases include Selenomonas, Prevotella, Treponema and Megasphaera. A purified and isolated DNA encoding a phytase of *Selenomonas ruminantium* JY35 (ATCC 55785) is provided. Recombinant expression vectors containing DNA's encoding the novel phytases and host cells transformed with DNA's encoding the novel phytases are also provided. The novel phytases are useful in a wide range of applications involving the dephosphorylation of phytate, including, among other things, use in animal feed supplements.

59 Claims, 14 Drawing Sheets

OTHER PUBLICATIONS

Scott, H.W. and Dehority, B.A. 1965. Vitamin Requirements of Several Celluloytic Bacteria. J. Bacteriol. 89:1169–1175.

Shieh, T.R. and Ware, J.H. 1968. Survey of Microorganisms for the Production of Extracellular Phytase, Appl. Microbiol. 16:1348–1351.

van Hartingsveldt, Wim, van Zeijl, C.M.J., Harteveld, G.M., Gouka, R.J., Suykerbuyk, M.E.G., Luiten, R.G.M., van Paridon, P.A., Selten, G.C.M., Veenstra, A.E., van Gorcum, R.F.M. and van den Hondel, C.A.M.J. 1993. Cloning, Characterization and Overexpression of the Phytase–Encoding Gene (phyA) of *Aspergillus niger*. Gene 127:87–94.

van Rooijen, Gijs J.H. and Moloney, M.M. 1994. Plant Seed Oil–Bodies as Carriers for Foreign Proteins. Bio/Technology 13:72–77.

von Heijne, Gunnar 1986. A New Method for Predicting Signal Sequence Cleavage Sites. Nucleic Acids Res. 14:4683–4690.

Wong, Sui–Lam 1989. Development of an Inducible and Enhancible Expression and Secretion System in *Bacillus subtilis*. Gene 83:215–223.

Dayhoff, M.O., Schwartz, R.M. and Orcutt, B.C. 1978. A Module of Evoluntionary Change in Proteins. In: Atlas of Protein Sequence and Structure. vol. 5. Supplement 3, 22:345–352.

Al–Asheh, S. and Z. Duvnjak. 1994. The Effect of Surfactants on the Phytase Production and the Reduction of the Phytic Content in Canola Meal by *Aspergillus carbonarius* During a Solid State Fermentation Process. Biotechnol. Lett. 16:183–188.

FIG. 15A

```
  1 CGTCCACGGA GTCACCCTAC TATACGACGT ATGTGAAGTT CACGTCGAAG TTCTAGGGAA   60
 61 TCACCGATTC GTGCAGGATT TTACCACTTC CTGTTGAAGC GGATGAGAAG GGGAACCGCG  120
121 AAGCGGGTGGA AGAGGTGCTG CACGACGGAC GATCGCGCTG AATGAATCAG TGCTTCCTAA  180
                                           R.B.S.
181 CTATTGGGAT TCCGCGCAGA CGGCGCGGATG GAGTAAAGGA GTAAGTTGTT ATG AAA TAC  239
                                                            M   K   Y    3
240 TGG CAG AAG CAT GCC GTT CTT TGT AGT CTC TTG GTC GGC GCA TCC CTC TGG  290
     W   Q   K   H   A   V   L   C   S   L   L   V   G   A   S   L   W   20
291 ATA CTG CCG CAG GCC GAT GCG GCC AAG GCG CCG GAG CAG GTG ACG GAG      341
     I   L   P   Q   A   D   A   A   K   A   P   E   Q   V   T   E      37
342 CCC GTT GGG AGC TAC GCG CGC GCG GAG CGG CCG CAG GAC TTC GAG GGC TTT  392
     P   V   G   S   Y   A   R   A   E   R   P   Q   D   F   E   G   F   54
393 GTC TGG CGC CTC GAC AAC GAC GAG AAG GAG GCG TTG CCG CGT AAT TTC CGC  443
     V   W   R   L   D   N   D   G   K   E   A   L   P   R   N   F   R   71
444 ACG TCG GCT GAC GCG CTG CGC GCG CCG GAG AAG AAA TTC CAT ATC TCG GGC GCC  494
     T   S   A   D   A   L   R   A   P   E   K   K   F   H   I   S   G   A   88
495 GCG TAT GTA CCG TCG CGC GAG GGC ATG GAT GCA CTC AAG AAC GTT GCC AAG CTG CGG GAG  545
     A   Y   V   P   S   R   E   G   M   D   A   L   K   N   V   A   K   L   R   E  105
546 TCC GCA TTC ACG GGC CCC ATC TAC GAT GTC GAC CTA CGG CAG GAG TCG CAC GGC  596
     S   A   F   T   G   P   I   Y   D   V   D   L   R   Q   E   S   H   G  122
597 AAG ACG GCT GGT ATC CCC GTG AGC TGG TAC GGC GAG CGC GGC GAG  647
     K   T   A   G   I   P   V   S   W   Y   G   E   R   G   E  139
648 TAT CTC GAC GGT ATC CCC GTG AGC TGG TAC GAC CGC GAC TGG GCA AAT  698
     Y   L   D   G   I   P   V   S   W   Y   D   R   D   W   A   N  156
```

FIG. 15B

```
699  CTC GGC AAG AGC CAG CAT GAG GCC GAC GAG CGG CAC CGC TTG CAC  749
157   L   G   K   S   Q   H   E   A   D   E   R   H   R   L   H   173

750  GCA GCG CTC CAT AAG ACG GTC TAC ATC GCG CCG CTC GGC AAG CTC  800
174   A   A   L   H   K   T   V   Y   I   A   P   L   G   K   L   190

801  CCC GAG GGC GGC GAA GTC CGC CGC GTA CAG AAG GTG CAG CAG GAA  851
191   P   E   G   G   E   V   R   R   V   Q   K   V   Q   Q   E   207

852  GTC GCC GAG GCC GCG GGG ATG CGC TAT TTC CGC ATC GCG GCG CAT  902
208   V   A   E   A   A   G   M   R   Y   F   R   I   A   A   H   224

903  GTC TGG CCA ACG CCG GAG AAC CGC TTC CTC GCG TTT TAC CGC ACG  953
225   V   W   P   T   P   E   N   R   F   L   A   F   Y   R   T   241

954  CTG CCG CAG GAT GCG GTC ATG GTC CAT TGT GAA GCC GGT GTC CGC  1004
242   L   P   Q   D   A   V   M   V   H   C   E   A   G   V   R   258

1005 ACG ACG GCG TTC ATG CTC ATG ACG GAT ATG CTG AAG ATG GGC GTA TCG  1055
259   T   T   A   F   M   L   M   T   D   M   L   K   M   G   V   S   275

1056 CTC AAG GAC ATC CCC ATC CTC AAG GAG ATC CAT TTC CAT AGC CCG TCC TTT  1106
276   L   K   D   I   P   I   L   K   E   I   H   F   H   S   P   S   F   292

1107 GAG TTC CCC AAG GTG ATC TAT CGC AAG GAT AAA CAG GAT AGC TGG AAG ACG  1157
293   E   F   P   K   V   I   Y   R   K   D   K   Q   D   S   W   K   T   309

1158 AGG GAA AAG GCG TAC GGC GAT GGC CAG TCG ATG ATC GAG TTC TAC CGC TAT GTG CAG AAC  1208
310   R   E   K   A   Y   G   D   G   Q   S   M   I   E   F   Y   R   Y   V   Q   N   326

1209 CGC GCG GAT GGC TAA AAGGCGAGGC  1259
327   R   A   D   G   *                    343

1260 GCG AAG GCG TAA AAGGCGAGGC GGGGGCTCGG AGTCAGGGAA ATGGCGCTGC  1311
344   A   K   A   *                                                346

1312 CAGCACGGGA CGGCGGGCCG CGGATGCTGC GCCGGTCAGG GATGATTGAC GACAGCCAGA  1371

1372 GAAGAAAGGA TGGTTTTATG AGGTGGATCC                             1401
```

_5,985,605_

DNA SEQUENCES ENCODING PHYTASES OF RUMINAL MICROORGANISMS

This application is a continuation-in-part of U.S. patent application Ser. No. 08/744,779, filed Nov. 6, 1996, and also takes priority from Provisional Application No. 60/019,735, filed Jun. 14, 1996, under 35 U.S.C. §119(e). Both of these applications are incorporated in their entirety by reference herein.

FIELD OF THE INVENTION

This invention relates to phytases derived from ruminal microorganisms.

BACKGROUND OF THE INVENTION

Although the plant constituents of livestock feedstuffs are rich in phosphorus, inorganic phosphorus supplementation is required to obtain good growth performance of monogastric animals. Phytic acid (myo-inositol hexaphosphoric acid) generally occurs as a complex of calcium, magnesium and potassium salts and/or proteins, and is the predominant form of phosphorus in cereals, oil seeds, and legumes, and accounts for 1 to 3% of the seed dry weight and 60 to 90% of the total phosphorus present in seeds (Graf, 1986). However, monogastric animals (e.g., swine, poultry and fish) utilize phytate poorly or not at all because they are deficient in gastrointestinal tract enzymes capable of hydrolyzing phytate. Phytate passes largely intact through the upper gastrointestinal tract, where it may decrease the bioavailability of nutrients by chelating minerals (e.g., calcium and zinc), binding amino acids and proteins (Graf, 1986) and inhibiting enzymes. Phytate phosphorus in manure poses a serious pollution problem, contributing to eutrophication of surface waters in areas of the world where monogastric livestock production is intensive.

Production inefficiencies and phosphorus pollution caused by phytate may be effectively addressed by phytase supplementation of diets for monogastric animals. Phytases catalyze the hydrolysis of phytate to myo-inositol and inorganic phosphate, which are then absorbed in the small intestine. In addition to decreasing phosphorus supplementation requirements and reducing the amount of phytate pollutants released, phytases also diminish the antinutritional effects of phytate.

Phytases are produced in animal and plant (predominantly seeds) tissues and by a variety of microorganisms (U.S. Pat. No. 3,297,548; Shieh and Ware, 1968; Ware and Shieh, 1967). Despite the array of potential phytase sources, only soil fungi (*Aspergillus niger* or *Aspergillus ficuum*) are currently used for commercial production of phytase. The phytase produced by *A. ficuum* possesses greater specific activity (100 units/mg of protein (wherein units are defined as µmoles of phosphate released per minute)) and thermostability compared to those phytases that have been characterized from other microorganisms (European Patent Application No. 0,420,358 (van Gorcum et al., 1991) and U.S. Pat. No. 5,436,156 (van Gorcum et al., issued Jul. 25, 1995)). The *A. ficuum* phytase is an acid phytase and exhibits little activity above pH 5.5 (Howson and Davis, 1983; van Gorcum et al., 1991). Consequently, activity is limited to a relatively small region of the monogastric digestive tract, in which the pH ranges from 2–3 (in the stomach) to 4–7 (in the small intestine).

Although the idea of phytase supplementation of monogastric diets was proposed more than 25 years ago (U.S. Pat. No. 3,297,548, Ware and Shieh, 1967), the high cost of enzyme production has restricted the use of phytase in the livestock industry. In North America, supplemental phytase is generally more expensive than phosphorus supplements. In some circumstances, the cost of phytase utilization may be partially offset if the use of this enzyme also decreases the need for supplementation of a second nutrient such as calcium. The use of phytase in North America is likely to increase as swine and poultry populations increase and as public pressures force a reduction in pollution associated with livestock production. Higher costs of phosphorus supplements and legislation requiring the use of phytase have made the use of this supplement more common in Europe and parts of the Orient than in North America. Governments of the Netherlands, Germany, Korea and Taiwan have enacted or are enacting legislation to reduce the phosphorus pollution created by monogastric livestock production.

A more effective means of increasing phytase utilization is through cost reduction. The cost of phytase can be reduced by decreasing production costs and/or producing an enzyme with superior activity. Recent advances in biotechnology may revolutionize the commercial enzyme industry by offering alternative, cost effective methods of enzyme production. Application of recombinant DNA technology has enabled manufacturers to increase the yields and efficiency of enzyme production, and to create new products. The original source organism need no longer limit the production of commercial enzymes. Genes encoding superior enzymes can be transferred from organisms such as anaerobic bacteria and fungi, typically impractical for commercial production, into well characterized industrial microbial production hosts (e.g., Aspergillus and Bacillus spp.). As well, these genes may be transferred to novel plant and animal expression systems.

Unlike monogastric animals, ruminants (e.g., cattle, sheep) readily utilize the phosphorus in phytic acid. It has been demonstrated that phytases are present in the rumen, and it has been proposed that ruminants reared on high grain diets (rich in phytate) do not require dietary phosphorus supplementation due to these ruminal phytases. A single report has attributed this phytase production to ruminal microorganisms (Raun et al., 1956), but overall, the unique capacity of ruminants to utilize phytate has largely been ignored. Raun et al. (1956) prepared microbial suspensions by centrifugal sedimentation (Cheng et al., 1955). Those microbial suspensions were almost certainly contaminated with microscopic particles of plant material. Since plants produce phytases, the study was inconclusive as to whether plant phytases or microbial phytases produced the observed activity. Although Raun et al. have raised the possibility that ruminal phytase production may be attributable to ruminal microorganisms, this possibility has not been explored.

In view of the foregoing, there remains a need for low cost phytases having biochemical characteristics well suited for use in animal feed supplements.

SUMMARY OF THE INVENTION

The inventors have discovered that the rumen is a rich source of microorganisms which produce phytases having biochemical characteristics (such as temperature and pH stability, low metal ion sensitivity and high specific activity) desirable for industrial applications such as animal feed supplementation and inositol production. Ruminal microorganisms tolerate anaerobic conditions and may be either facultative or obligate anaerobes. Ruminal microorganisms may be prokaryotes (i.e. bacteria) or eukaryotes (i.e. fungi, protozoa). As used herein, the term "ruminal microorganisms" includes microorganisms isolated from the digesta or feces of a ruminant animal.

Ruminal bacterial species which have been identified as providing particularly active phytases includes *Selenomonas ruminantium*, Prevotella sp, *Treponema bryantii* and *Megaphaera elsdenii*. Prevotella and Selenomonas are Gram negative anaerobic rods from the family Bacteriodaceae.

In accordance with the present invention, DNA sequences encoding novel and useful phytases derived from ruminal microorganisms are provided.

A phytase gene (phyA) from *Selenomonas ruminantium* strain JY35 has been cloned and sequenced, and the nucleotide sequence of the phyA gene is provided. The invention extends to DNA sequences which encode phytases and which are capable of hybridizing under stringent conditions with the phyA gene sequence. As used herein, "capable of hybridizing under stringent conditions" means annealing to a subject nucleotide sequence, or its complementary strand, under standard conditions (ie. high temperature and/or low salt content) which tend to disfavor annealing of unrelated sequences. As used herein, "conditions of low stringency" means hybridization and wash conditions of 40–50° C., 6×SSC and 0.1% SDS (indicating about 50–80% homology). As used herein, "conditions of medium stringency" means hybridization and wash conditions of 50–65° C., 1×SSC and 0.1% SDS (indicating about 80–95% homology). As used herein, "conditions of high stringency" means hybridization and wash conditions of 65–68° C., 0.1×SSC and 0.1% SDS (indicating about 95–100% homology).

As used herein, the term "phytase" means an enzyme capable of catalyzing the removal of inorganic phosphorus from a myo-inositol phosphate.

As used herein, the term "myo-inositol phosphate" includes, without limitation, myo-inositol hexaphosphate, myo-inositol pentaphosphate, myo-inositol tetraphosphate, myo-inositol triphosphate, myo-inositol diphosphate and myo-inositol monophosphate.

As used herein, "phytate" means the salt of myo-inositol hexaphosphoric acid.

The invention extends to the *S. ruminantium* JY35 (ATCC 55785) organism itself, and to methods for identifying and isolating this and other ruminal microorganisms exhibiting phytase activity as well as methods for isolating, cloning and expressing phytase genes from ruminal microorganisms exhibiting phytase activity using part or all of the phyA gene sequence as a probe.

The invention further extends to methods for assaying phytase production by a microorganism whereby false positive results caused by microbial acid production are eliminated. Colonies of microorganisms are grown on a growth medium containing phytate. The medium is contacted with an aqueous solution of cobalt chloride and the medium is then examined for zones of clearing. Preferably, rather than examining the medium immediately, the solution of cobalt chloride is removed and the medium is contacted with aqueous solutions of ammonium molybdate and ammonium vanadate and then examined for zones of clearing. False positive results which occur when acid-forming microbes produce zones of clearing are avoided.

The invention extends to expression constructs constituting a DNA encoding a phytase of the present invention operably linked to control sequences capable of directing expression of the phytase in a suitable host cell.

The invention further extends to host cells which have been transformed with, and express, DNA encoding a phytase of the present invention, and to methods of producing such transformed host cells. As used herein "host cell" includes animal, plant, yeast, fungal, protozoan and prokaryotic host cells.

The invention further extends to transgenic plants which have been transformed with a DNA encoding a phytase of the present invention so that the transformed plant is capable of expressing the phytase and to methods of producing such transformed plants. As used herein, "transgenic plant" includes transgenic plants, tissues and cells.

Phytases of the present invention are useful in a wide variety of applications involving the dephosphorylation of phytate. Such applications include use in animal feed supplements, feedstuff conditioning, human nutrition, and the production of inositol from phytic acid. Phytases of the present invention may also be used to minimize the adverse effects of phytate metal chelation. The high phytate content of certain feedstuffs such as soy meal decreases their value as protein sources for fish, monogastric animals, young ruminants and infants because the phytate decreases the bioavailability of nutrients by chelating minerals, and binding amino acids and proteins. Treatment of such feedstuffs with the phytases of the present invention will reduce their phytate content by phytase mediated dephosphorylation, rendering the feedstuffs more suitable for use as protein sources. Accordingly, the invention extends to novel feed compositions comprising feedstuffs treated with a phytase of the present invention, and feed additives containing a phytase of the present invention. Such feed compositions and additives may also contain other enzymes, such as, proteases, cellulase, xylanases and acid phosphatases. The phytase may be added directly to an untreated, pelletized, or otherwise processed feedstuff, or it may be provided separately from the feedstuff in, for instance, a mineral block, a pill, a gel formulation, a liquid formulation, or in drinking water. The invention extends to feed inoculant preparations comprising lyophilized microorganisms which express phytases of the present invention under normal growing conditions. With respect to these feed inoculant preparations, "normal growing conditions" mean culture conditions prior to harvesting and lyophilization of the microorganisms. The microorganisms express phytases during growth of the microbial cultures in large-scale fermenters. The activity of phytases in the microorganisms is preserved by lyophilization of the harvested microbial concentrates containing the phytase.

The invention further extends to a method for improving an animal's utilization of dietary phosphate by feeding the animal an effective amount of a phytase of the present invention. As used herein "an effective amount" of a phytase means an amount which results in a statistically significant improvement in phosphorus utilization by the animal. Phytate phosphorus utilization may be evidenced by, for instance, improved animal growth and reduced levels of phytate in animal manure.

BRIEF DESCRIPTION OF DRAWINGS

FIGS. 15A and 15B are the nucleotide sequence of the *S. ruminantium* JY35 phytase gene (phyA) (SEQ ID NO. 1) and its deduced amino acid sequence (SEQ ID NO. 2). Nucleotide 1 corresponds to nt 1232 of the 2.7-kb insert of pSrP.2. The putative ribosome binding site is underlined and shown above the sequence as R.B.S. The signal peptidase cleavage site, predicted by the method of von Heijne (1986) is indicated by the ↑. The N-terminal amino acid sequence of the phytase secreted by *E. coli* (pSrPf6) is underlined.

DETAILED DESCRIPTION OF THE PREFERRED EMBODIMENT

The rumen is a complex ecosystem inhabited by more than 300 species of bacteria, fungi and protozoa. Screening these organisms for phytase activity requires the ability to discriminate the phytase activity of individual isolates. This may be accomplished through the assessment of pure cultures from a stock culture collection or separation and cultivation of individual cells through cultural techniques (e.g., streak plate, dilution and micromanipulation). Standard aseptic, anaerobic techniques described for bacteria, fungi and protozoa may be used to accomplish this goal.

Suitable enzyme assays are necessary for screening microbial isolates in ruminal fluid samples and from culture collections, and for cloning phytase genes. Assays for measuring phytase activity in solutions have been described in the literature. Sample solutions are typically assayed for phytase activity by measuring the release of inorganic phosphorus ($P_i$) from phytic acid (Raun et al., 1956; van Hartingsveldt et al., 1993). Phytase activity may also be detected on solid media. Microorganisms expressing phytase produce zones of clearing on agar media containing sodium or calcium phytate (Shieh and Ware, 1968; Howson and Davis, 1983). However, the solid media assays described in the literature were found to be unsatisfactory for screening ruminal bacteria for phytase activity because of the false positive reactions of acid-producing bacteria such as *Streptococcus bovis*. To overcome this problem, a two-step counterstaining procedure was developed in which petri dishes containing solid medium are flooded first with an aqueous cobalt chloride solution and second with an aqueous ammonium molybdate/ammonium vanadate solution. Following this treatment only clearing zones produced by enzyme activity are evident (FIG. 1).

Using the above solutions and solid medium assays, 345 isolates from the Lethbridge Research Centre (Lethbridge, Alberta, Canada) culture collection were screened for phytase activity (Table 1). A total of 29 cultures with substantial phytase activity were identified, including 24 of the genus Selenomonas and 5 of the genus Prevotella. Twelve of these cultures (11 Selenomonas isolates and 1 Prevotella isolate) had phytase activities substantially higher than the other positive cultures (Table 2).

The phytase of *S. ruminantium* JY35 (deposited May 24, 1996 with the American Type Culture Collection, 12301 Parklawn Drive, Rockville, Md., 20852-1776, as ATCC 55785) was selected for further examination and compared to a commercial phytase (Gist-brocades nv, Delft, The Netherlands) from *Aspergillus ficuum* NRRL 3135 (van Gorcum et al., 1991 and 1995). The phytase of *S. ruminantium* JY35 (ATCC 55785) is constitutively expressed, exported from the cell and associated with the cell surface. The pH (FIG. 5) and temperature (FIG. 6) profiles of the *S. ruminantium* JY35 (ATCC 55785) phytase were comparable, if not more suited to industrial production, than are those of the commercial *A. ficuum* NRRL 3135 phytase. These results demonstrated the potential of ruminal and anaerobic microbes as sources of phytases with characteristics superior to phytases currently being produced by industry.

Microbial genes encoding selected enzymes can be cloned by a variety of methods. Gene libraries (genomic DNA and/or cDNA) are constructed by standard methods (Sambrook et al., 1989; Ausubel et al., 1990) and screened for the desired gene. The screening methodology may utilize heterologous probes, enzyme activity or results generated during purification of the gene product, such as N-terminal and internal amino acid sequence data and antibodies.

Using the solid medium phytase assay developed to detect phytase activity produced by ruminal microbes, a *S. rumi-*

Figure 1:
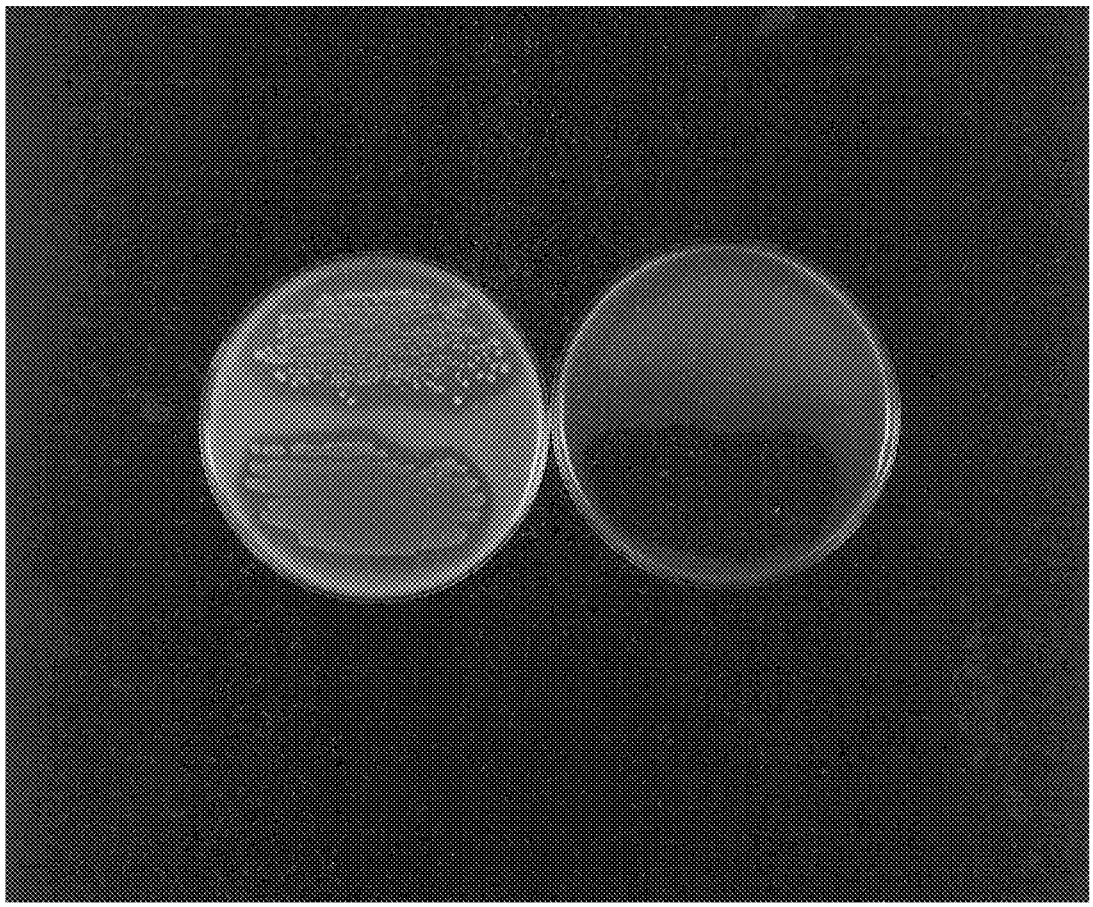
FIG. 1 is a photograph showing the effect of counterstaining agar medium containing phytate on zones of clearing produced by acid production or phytase activity. Phytate agar was inoculated with *S. bovis* (top of left petri dish) and *S. ruminantium* JY35 (bottom of left petri dish) and incubated for 5 d at 37° C. The colonies were scraped off and the medium counterstained with cobalt chloride and ammonium molybdate/ammonium vanadate solutions (right petri plate).

nantium JY35 (ATCC 55785) gene library was screened for positive clones. Of 6000 colonies examined, a single colony was identified as a phytase positive clone by a large zone of clearing around the colony. This clone carried a 5.5-kb plasmid comprising a 2.7-kb Sau3A DNA fragment inserted into cloning vector pUC18. The newly isolated 2.7-kb Sau3A DNA fragment was used as a probe in Southern blot hybridizations. Under high stringency conditions, a discrete band could be detected for *S. ruminantium* isolate JY35 (ATCC 55785), but not for Prevotella sp. 46/5$^2$, *E. coli* DH5α or *A. ficuum* NRRL 3135.

Plasmid DNA isolated from the newly isolated clone and introduced into *E. coli* cells by transformation produced ampicillin-resistant, phytase-positive CFUs. Zymogram analysis of cell extracts from *E. coli* DH5α cells carrying the 2.7-kb Sau3A DNA fragment from *S. ruminantium* JY35 (ATCC 55785) revealed a single activity band with an estimated molecular mass of 37 kDa. Deletion and DNA sequence analyses were used to identify the gene (phyA) which encoded the phytase responsible for the activity observed in recombinant *E. coli* clones. The N-terminal amino acid sequence of the purified 37-kDa phytase expressed in *E. coli* cells carrying phyA matched the N-terminal amino acid sequence of the mature phytase predicted from the cloned phyA sequence. This indicated conclusively that the nucleotide sequence encoding the phytase had been isolated. The nucleotide sequence and deduced amino acid sequence are shown in FIGS. 15A and 15B.

As with other genes, it is possible to use the characterized phytase coding sequence in a variety of expression systems for commercial enzyme production. Application of recombinant DNA technology has enabled enzyme manufacturers to increase the volume and efficiency of enzyme production, and to create new products. The original source organism need no longer limit the production of commercial enzymes. Genes encoding superior enzymes can be transferred from organisms such as anaerobic bacteria and fungi, typically impractical for commercial production, into well characterized industrial microbial production hosts (e.g., Aspergillus, Pichia, Trichoderma, Bacillus spp.). As well, these genes may be transferred to novel plant and animal expression systems.

Industrial strains of microorganisms (e.g., *Aspergillus niger, Aspergillus ficuum, Aspergillus awamori, Aspergillus oryzae, Trichoderma reesei, Mucor miehei, Kluyveromyces lactis, Pichia pastoris, Saccharomyces cerevisiae, Escherichia coli, Bacillus subtilis* or *Bacillus licheniformis*) or plant hosts (e.g., canola, soybean, corn, potato) may be used to produce phytase. All systems employ a similar approach to gene expression. An expression construct is assembled to include the protein coding sequence of interest and control sequences such as promoters, enhancers and terminators. Other sequences such as signal sequences and selectable markers may also be included. To achieve extracellular expression of phytase, the expression construct of the present invention utilizes a secretory signal sequence. The signal sequence is not included on the expression construct if cytoplasmic expression is desired. The promoter and signal sequence are functional in the host cell and provide for expression and secretion of the coding sequence product. Transcriptional terminators are included to ensure efficient transcription. Ancillary sequences enhancing expression or protein purification may also be included in the expression construct.

The protein coding sequences for phytase activity are obtained from ruminal microbial sources. This DNA may be homologous or heterologous to the expression host. Homologous DNA is herein defined as DNA originating from the same species. For example, *S. ruminantium* may be transformed with DNA from *S. ruminantium* to improve existing properties without introducing properties that did not exist previously in the species. Heterologous DNA is defined as DNA originating from a different species. For example, the *S. ruminantium* phyA may be cloned and expressed in *E. coli.*

It is well known in the biological arts that certain amino acid substitutions can be made in protein sequences without affecting the function of the protein. Generally, conservative amino acid substitutions are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure*, Volume 5, Supplement 3, Chapter 22, pages 345–352, which is incorporated by reference herein, provides frequency tables for amino acid substitutions which can be employed as a measure of amino acid similarity. Dayoff et al.'s frequency tables are based on comparisons of amino acid sequences for proteins having the same function from a variety of evolutionary different sources.

It is also well-known that often less than a full length protein has the function of the complete protein, for example, a truncated protein lacking an N-terminal, internal or a C-terminal protein often ha the biological and/or enzymatic activity of the complete natural protein. Gene truncation experiments involving phyA have confirmed that the truncated protein may retain the function of the intact protein. *Exherichia coli* clones expressing PhyA missing N-terminal amino acids 1–37 or 1058 (SEQ ID NO. 2) showed phytase positive phenotypes. In contrast, no phytase activity could be detected for a clone expressing PhyA missing acids 307–346 (SEQ ID NO. 2). Those of ordinary skill in the art know how to make truncated protein and proteins with internal deletions. In the present invention, the function of a truncated phytase protein or an internally deleted phytase protein can be readily tested using the assay described hereinbelow and n view of what is generally known in the art.

Substituted, internally-deleted and truncated rumina phytase derivatives which retain substantially the same enzymatic activity as a phytase specifically disclosed herein are considered equivalents of the exemplified phytase and are within the scope of the present invention, particularly where the specific activity of the substituted, internally-deleted or truncated phytase derivative is at least about 10% of the specifically exemplified phytase. The skilled artisan can readily measure the activity of a rumina phytase, truncated phytase, internally-deleted phytase or substituted phytase using the assay procedures taught herein and in view of what is generally known in the art.

This invention includes structurally variant phytases derived from a phytase of a rumina microorganisms, particularly those derived from a phytase specifically disclosed herein, that are substantially functionally equivalent to that phytase as assayed as described herein in view of what is generally known in the art. Structurally variant, functional equivalents of the phytases of this invention include those phytase of rumina microorganisms having a contiguous amino acid sequence as in the phytase amino acid sequence disclosed herein (SEQ ID NO. 2), particularly those variant phytase which have a contiguous amino acid sequence of a phytase of a rumina microorganism that is a contiguous sequence at least about 25 amino acids in length.

The present invention also provides the starting material for the construction of phytases with properties that differ from those of the enzymes isolated herein. The genes can be readily mutated by known procedures (e.g., chemical, site directed, random polymerase chain reaction mutagenesis) thereby creating gene products with altered properties (e.g., temperature or pH optima, specific activity or substrate specificity).

Various promoters (transcriptional initiation regulatory region) may be used according to the present invention. The selection of the appropriate promoter is dependent upon the proposed expression host. Choices of promoters may include the promoter associated with the cloned protein coding sequence or promoters from heterologous sources as long as they are functional in the chosen host. Examples of heterologous promoters are the *E. coli* tac and trc promoters (Brosius et al., 1985), *Bacillus subtilis* sacB promoter and signal sequence (Wong, 1989), aox1 and aox2 from *Pichia pastoris* (Ellis et al., 1985), and oleosin seed specific promoter from *Brassica napus* or *Arabidopsis thaliana* (van Rooijen and Moloney, 1994). Promoter selection is also dependent upon the desired efficiency and level of peptide or protein production. Inducible promoters such tac and aox1 are often employed in order to dramatically increase the level of protein expression. Overexpression of proteins may be harmful to the host cells. Consequently, host cell growth may be limited. The use of inducible promoter systems allows the host cells to be cultivated to acceptable densities prior to induction of gene expression, thereby facilitating higher product yields. If the protein coding sequence is to be integrated through a gene replacement (omega insertion) event into a target locus, then promoter selection may also be influenced by the degree of homology to the target locus promoter.

Various signal sequences may be used according to the present invention. A signal sequence which is homologous to the protein coding sequence to be expressed may be used. Alternatively, a signal sequence which has been selected or designed for improved secretion in the expression host may also be used. For example, *B. subtilis* sacB signal sequence for secretion in *B. subtilis*, the *Saccharomyces cerevisiae* α-mating factor or *P. pastoris* acid phosphatase pho1 signal sequences for *P. pastoris* secretion may be used. A signal sequence with a high degree of homology to the target locus may be required if the protein coding sequence is to be integrated through an omega insertion event. The signal sequence may be joined directly through the sequence encoding the signal peptidase cleavage site to the protein coding sequence, or through a short nucleotide bridge consisting of usually fewer than ten codons.

Elements for enhancing expression transcription (promoter activity) and translation have been identified for eukaryotic protein expression systems. For example, positioning the cauliflower mosaic virus (CaMV) promoter 1000 bp on either side of a heterologous promoter may elevate transcriptional levels by 10- to 400-fold. The expression construct should also include the appropriate translational initiation sequences. Modification of the expression construct to include the Kozak consensus sequence for proper translational initiation may increase the level of translation by 10 fold.

Elements to enhance purification of the protein may also be included in the expression construct. The product of oleosin gene fusions is a hybrid protein containing the oleosin gene joined to the gene product of interest. The fusion protein retains the lipophilic properties of oleosins and is incorporated in the oil body membranes (van Rooijen and Moloney, 1994). Association with the oil bodies may be exploited to facilitate purification of the recombinant oleosin fusion proteins (van Rooijen and Moloney, 1994).

A selection marker is usually employed, which may be part of the expression construct or separate from it (e.g., carried by the expression vector), so that the marker may integrate at a site different from the gene of interest. Transformation of the host cells with the recombinant DNA molecules of the invention is monitored through the use of selectable markers. Examples of these are markers that confer resistance to antibiotics (e.g., bla confers resistance to ampicillin for *E. coli* host cells, nptII confers kanamycin resistance to *B. napus* cells) or that permit the host to grow on minimal medium (e.g., HIS4 enables *P. pastoris* GS115 His⁻ to grow in the absence of histidine). The selectable marker will have its own transcriptional and translational initiation and termination regulatory regions to allow for independent expression of the marker. Where antibiotic resistance is employed as a marker, the concentration of the antibiotic for selection will vary depending upon the antibiotic, generally ranging from 10 to 600 µg of the antibiotic/mL of medium.

The expression construct is assembled by employing known recombinant DNA techniques. Restriction enzyme digestion and ligation are the basic steps employed to join two fragments of DNA. The ends of the DNA fragment may require modification prior to ligation and this may be accomplished by filling in overhangs, deleting terminal portions of the fragment(s) with nucleases (e.g., ExoIII), site directed mutagenesis, and adding new base pairs by the polymerase chain reaction (PCR). Polylinkers and adaptors may be employed to facilitate joining of select fragments. The expression construct is typically assembled in stages employing rounds of restriction, ligation and transformation of *E. coli*. There are numerous cloning vectors available for construction of the expression construct and the particular choice is not critical to this invention. The selection of cloning vector will be influenced by the gene transfer system selected for introduction of the expression contruct into the host cell. At the end of each stage, the resulting construct may be analyzed by restriction, DNA sequence, hybridization and PCR analyses.

The expression construct may be transformed into the host as the cloning vector construct, either linear or circular, or may be removed from the cloning vector and used as is or introduced onto a delivery vector. The delivery vector facilitates the introduction and maintenance of the expression construct in the selected host cell type. The expression construct is introduced into the host cells by employing any of a number of gene transfer systems (e.g., natural competence, chemically mediated transformation, protoplast transformation, electroporation, biolistic transformation, transfection, or conjugation). The gene transfer system selected depends upon the host cells and vector systems used.

For instance, the expression construct can be introduced into *P. pastoris* cells by protoplast transformation or electroporation. Electroporation of *P. pastoris* is easily accomplished and yields transformation efficiencies comparable to spheroplast transformation. *P. pastoris* cells are washed with sterile water and resuspended in a low conductivity solution (e.g., 1 M sorbitol solution). A high voltage shock applied to the cell suspension creates transient pores in the cell membrane through which the transforming DNA (e.g., expression construct) enters the cells. The expression construct is stably maintained by integration, through homologous recombination, into the aox1 (alcohol oxidase) locus.

Alternatively, an expression construct, comprising the sacB promoter and signal sequence operably linked to the protein coding sequence, is carried on pUB110, a plasmid capable of autonomously replicating in *B. subtilis* cells. The resulting plasmid construct is introduced into *B. subtilis* cells by transformation. *Bacillus subtilis* cells develop natural competence when grown under nutrient poor conditions.

In a third example, *Brassica napus* cells are transformed by Agrobacterium-mediated transformation. The expression construct is inserted onto a binary vector capable of replication in *A. tumefaciens* and mobilization into plant cells. The resulting contruct is transformed into *A. tumefaciens* cells carrying an attenuated Ti or "helper plasmid". When leaf disks are infected with the recombinant *A. tumefaciens* cells, the expression construct is transferred into *B. napus* leaf cells by conjugal mobilization of the binary vector::expression construct. The expression construct integrates at random into the plant cell genome.

Host cells carrying the expression construct (i.e., transformed cells) are identified through the use of the selectable marker carried by the expression construct or vector and the presence of the gene of interest confirmed by a variety of techniques including hybridization, PCR, and antibodies.

The transformant microbial cells may be grown by a variety of techniques including batch and continuous fermentation on liquid or semi-solid media. Transformed cells are propagated under conditions optimized for maximal product-to-cost ratios. Product yields may be dramatically increased by manipulating of cultivation parameters such as temperature, pH, aeration, and media composition. Careful manipulation and monitoring of the growth conditions for recombinant hyper-expressing *E. coli* cells may result in culture biomass and protein yields of 150 g (wet weight) of cells/L and 5 g of insoluble protein/L, respectively. Low concentrations of a protease inhibitor (e.g., phenylmethylsulfonyl fluoride or pepstatin) may be employed to reduce proteolysis of the over-expressed peptide or protein. Alternatively, protease deficient host cells may be employed to reduce or eliminate degradation of the desired protein.

After selection and screening, transformed plant cells can be regenerated into whole plants and varietal lines of transgenic plants developed and cultivated using known methods. As used herein, "transgenic plant" includes transgenic plants, plant tissues and plant cells.

Following fermentation, the microbial cells may be removed from the medium through down-stream processes such as centrifugation and filtration. If the desired product is secreted, it can be extracted from the nutrient medium. In the case of intracellular production, the cells are harvested and the product released by rupturing cells through the application of mechanical forces, ultrasound, enzymes, chemicals and/or high pressure. Production of an insoluble product, such as occurs in hyper-expressing *E. coli* systems, can be used to facilitate product purification. The product inclusions can be extracted from disrupted cells by centrifugation and contaminating proteins may be removed by washing with a buffer containing low concentrations of a denaturant (e.g., 0.5 to 6 M urea, 0.1 to 1% sodium dodecyl sulfate or 0.5 to 4.0 M guanidine-HCl). The washed inclusions may be solubilized in solutions containing 6 to 8 M urea, 1 to 2% sodium dodecyl sulfate or 4 to 6 M guanidine-HCl. Solubilized product can be renatured by slowly removing denaturing agents during dialysis.

Phytase may be extracted from harvested portions or whole plants by grinding, homogenization, and/or chemical treatment. The use of seed specific lipophilic oleosin fusions can facilitate purification by partitioning the oleosin fusion protein in the oil fraction of crushed canola seeds, away from the aqueous proteins (van Rooijen and Moloney, 1994).

If necessary, various methods for purifying the product, from microbial, fermentation and plant extracts, may be employed. These include precipitation (e.g., ammonium sulfate precipitation), chromatography (gel filtration, ion exchange, affinity liquid chromatography), ultrafiltration, electrophoresis, solvent-solvent extraction (e.g., acetone precipitation), combinations thereof, or the like.

All or a portion of the microbial cultures and plants may be used directly in applications requiring the action of phytase. Various formulations of the crude or purified phytase preparations may also be prepared. The enzymes can be stabilized through the addition of other proteins (e.g., gelatin, skim milk powder) and chemical agents (e.g., glycerol, polyethylene glycol, reducing agents and aldehydes). Enzyme suspensions can be concentrated (e.g., tangential flow filtration) or dried (spray and drum drying, lyophilization) and formulated as liquids, powders, granules, pills, mineral blocks and gels through known processes. Gelling agents such as gelatin, alginate, collagen, agar, pectin and carrageenan may be used.

Further, complete dephosphorylation of phytate may not be achieved by phytase alone. Phytases may not dephosphorylate the lower myo-inositol phosphates. For instance, an *A. ficuum* phytase described in U.S. Pat. No. 5,536,156 (van Gorcum et. al., issued Jul. 25, 1995) exhibits low or no phosphatase activity against myo-inositol di-phosphate or myo-inositol mono-phosphate. Addition of another phosphatase, such as an acid phosphatase, to a feed additive of the present invention containing phytase will help dephosphorylate myo-inositol di-phosphate and myo-inositol mono-phosphate.

Formulations of the desired product may be used directly in applications requiring the action of a phytase. Liquid concentrates, powders and granules may be added directly to reaction mixtures, fermentations, steeping grains, and milling waste. The formulated phytase can be administered to animals in drinking water, in a mineral block, as a salt, or as a powdered supplement to be sprinkled into feed bunks or mixed with a ration. It may also be mixed with, sprayed on or pelleted with other feed stuffs through known processes. Alternatively, a phytase gene with a suitable promoter-enhancer sequence may be intergrated into an animal genome and selectively expressed in an organ or tissue (e.g. salivary glands, pancreas or epithelial cells) which secrete the phytase enzyme into the gastrointestinal tract, thereby eliminating the need for the addition of supplemental phytase.

In a preferred formulation, phytases of the present invention may take the form of microbial feed inoculants. Cultures of microorganisms expressing a native phytase, such as *S. ruminantium* JY35 (ATCC 55785), or recombinant microorganisms expressing a phytase encoded by a heterologous phytase gene are grown to high concentrations in fermenters and then harvested and concentrated by centrifugation. Food-grade whey and/or other cryoprotective agents are then admixed with the cell concentrate. The resulting mixture is then cryogenically frozen and freeze-dried to preserve phytase activity by standard lyophilization procedures. The freeze-dried culture may be further processed to form a finished product by such further steps as blending the culture with an inert carrier to adjust the strength of the product.

All or a portion of the microbial cultures and plants as produced by the present invention may be used in a variety of industrial processes requiring the action of a phytase. Such applications include, without limitation, the manufacture of end products such as inositol phosphate and inositol, production of feed ingredients and feed additives for non-ruminants (e.g., swine, poultry, fish, pet food), in human nutrition, and in other industries (soybean and corn processing, starch, and fermentation) that involve feedstocks containing phytate. Degradation of phytate makes inorganic phosphate and chelated metals available to animals and microorganisms. The action of phytase increases the quality, value and utility of feed ingredients and/or fermentation substrates that are high in phytate. The action of phytases can also accelerate the steeping process and separation processes involved in the wet milling of corn.

The phytase genes of the present invention can be used in heterologous hybridization and polymerase chain reaction experiments, directed to isolation of phytase encoding genes from other microorganisms. The examples herein are given by way of illustration and are in no way intended to limit the scope of the present invention. Efforts have been made to ensure the accuracy with respect to numbers used (e.g., temperature, pH, amounts) but the possibility of some experimental variance and deviations should be recognized.

EXAMPLE 1

Isolation of Ruminal Bacteria

Ruminal fluid from a cannulated Holstein cow was collected in a sterile Whirlpak™ bag. Fluid may also be withdrawn from the rumen via an orogastric tube. Under a suitable anaerobic atmosphere (e.g., 90% $CO_2$ and 10% $H_2$), ten-fold serial dilutions of the rumen fluid were prepared and distributed over the surface of a solid growth medium (e.g., Scott and Dehority, 1965), and the plates were incubated at 39° C. for 18 to 72 h. Isolated colonies were picked with a sterile loop and the cells were spread over the surface of fresh agar medium to produce isolated colonies. The cells from a single colony were confirmed by morphological examination to represent a pure culture and were cultured and stored in the Lethbridge Research Centre ("LRC") culture collection or used as a source of enzymatic activity or genetic material.

EXAMPLE 2

Screening Ruminal Bacteria for Phytase Activity

A. Phytase assays

Sample solutions (culture filtrates, cell suspensions, lysates, washes or distilled water blanks) were assayed for phytase activity by incubating 150 μl of the solution with 600 μl of substrate solution [0.2% (w/v) sodium phytate in 0.1 M sodium acetate buffer, pH 5.0] for 30 min at 37° C. The reaction was stopped by adding 750 μl of 5% (w/v) trichloroacetic acid. Released orthophosphate in the reaction mixture was measured by the method of Fiske and Subbarow (1925). Freshly prepared colour reagent [750 μl of a solution containing 4 volumes of 1.5% (w/v) ammonium molybdate in a 5.5% (v/v) sulfuric acid solution and 1 volume of a 2.7% (w/v) ferrous sulfate solution] was added to the reaction mixture and the production of phosphomolybdate was measured spectrophotometrically at 700 nm. Results were compared to a standard curve prepared with inorganic phosphate. One unit ("Unit") of phytase was defined as the amount of enzyme required to release one μmole of inorganic phosphate ($P_i$) per min under the assay conditions.

An improved phytase plate assay was developed which eliminated false positive results caused by microbial acid production. Bacterial isolates were grown under anaerobic conditions on modified Scott and Dehority (1965) agar medium containing 5% (v/v) rumen fluid, 1.8% (w/v) agar and 2.0% (w/v) sodium phytate for 5 d at 37° C. Colonies were washed from the agar surface and the petri plates were flooded with a 2% (w/v) aqueous cobalt chloride solution. After a 5-min incubation at room temperature the cobalt chloride solution was replaced with a freshly prepared solution containing equal volumes of a 6.25% (w/v) aqueous ammonium molybdate solution and 0.42% (w/v) ammonium vanadate solution. Following a 5-min incubation, the ammonium molybdate solution/ammonium vanadate solution was removed and the plates examined for zones of clearing. The effectiveness of this counterstaining technique is demonstrated in FIG. 1. Prior to staining, zones of clearing were evident around colonies of phytase-producing *S. ruminantium* JY35 (ATCC 55785) and lactic acid-producing *S. bovis* grown on agar medium containing phytate (FIG. 1, left petri plate). The false positive zones of clearing resulting from acid production by *S. bovis* colonies were eliminated by counterstaining the plates with cobalt chloride and ammonium molybdate/ammonium vanadate solutions (FIG. 1, right petri plate).

B. Phytase Activity of Ruminal Bacteria

The phytase activities of 345 rumen bacteria from the LRC culture collection were determined (Table 1). The anaerobic technique of Hungate (1950), as modified by Bryant and Burkey (1953), or an anaerobic chamber with a 90% $CO_2$ and 10% $H_2$ atmosphere was used to cultivate the microorganisms in the LRC culture collection. Phytase screening was performed on isolates grown anaerobically (100% $CO_2$) in Hungate tubes with 5 mL of modified Scott and Dehority medium (1965) containing 5% (v/v) rumen fluid, 0.2% (w/v) glucose, 0.2% (w/v) cellobiose and 0.3% (w/v) starch. After 18 to 24 h incubation at 39° C., whole cells or culture supernatants were assayed for phytase activity. Selenomonads were the predominant phytase producers (93% of the isolates tested had phytase activity, Table 1). Prevotella was the only other genus from which a significant number of positive cultures was identified (11 phytase positive isolates out of 40 tested). A total of 29 cultures with substantial phytase activity were identified. These included 24 of the genus Selenomonas and 5 of the genus Prevotella. Twelve of these cultures (11 Selenomonas and 1 Prevotella isolate) had phytase activities substantially higher than the other positive cultures (Table 2). In all instances, the phytase activity was predominantly cell associated.

EXAMPLE 3

Phytase Activity of *Selenomonas ruminantium* JY35 (ATCC 55785)

A. Growth and phytase production

Figure 2:
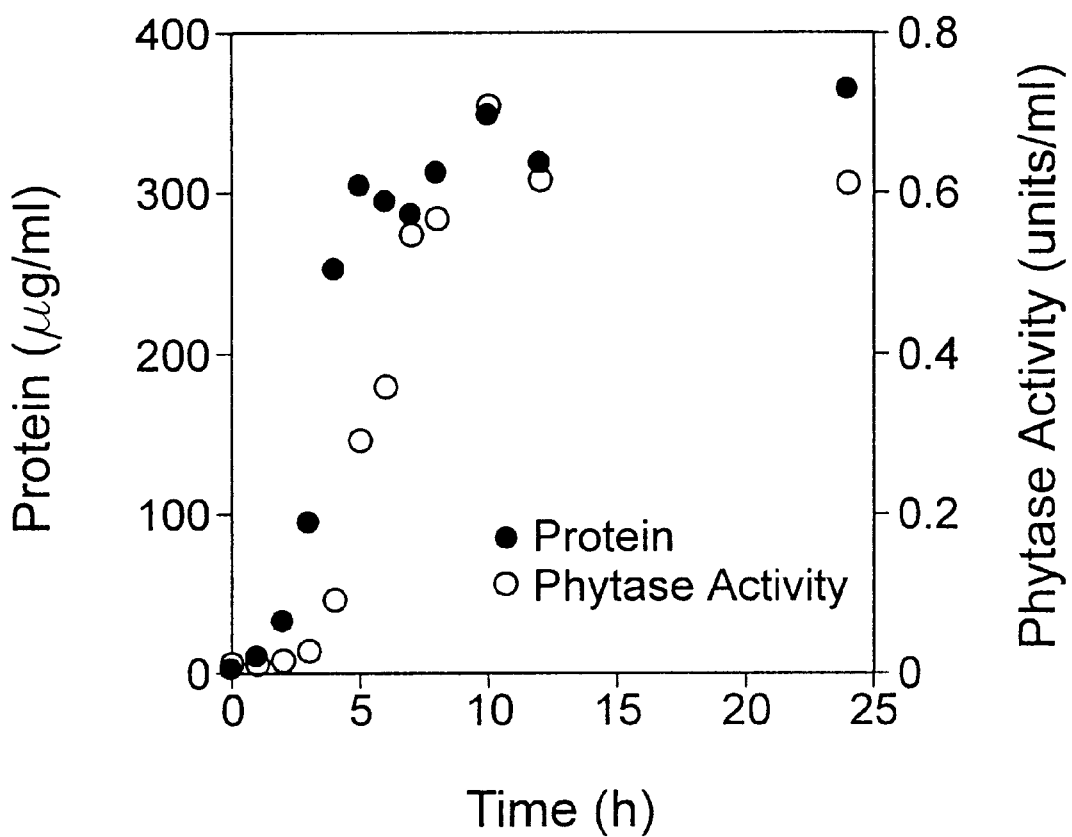
FIG. 2 is a graph illustrating the growth (protein) and phytase production of *S. ruminantium* JY35 in modified Scott and Dehority (1965) broth.

Phytase production during growth of *S. ruminantium* JY35 (ATCC 55785) was examined. *S. ruminantium* JY35 (ATCC 55785) was grown at 39° C. in Hungate tubes with 5 mL of modified Scott and Dehority broth (1965) containing 5% (v/v) ruminal fluid. Growth (protein concentration) and phytase activity (cell associated) were monitored at intervals over a 24-h time period. Maximal growth and phytase activity of *S. ruminantium* JY35 (ATCC 55785) were achieved 8–10 h after inoculation (FIG. 2). Cell growth was mirrored by increases in phytase activity.

B. Localization of phytase activity

Figure 3:
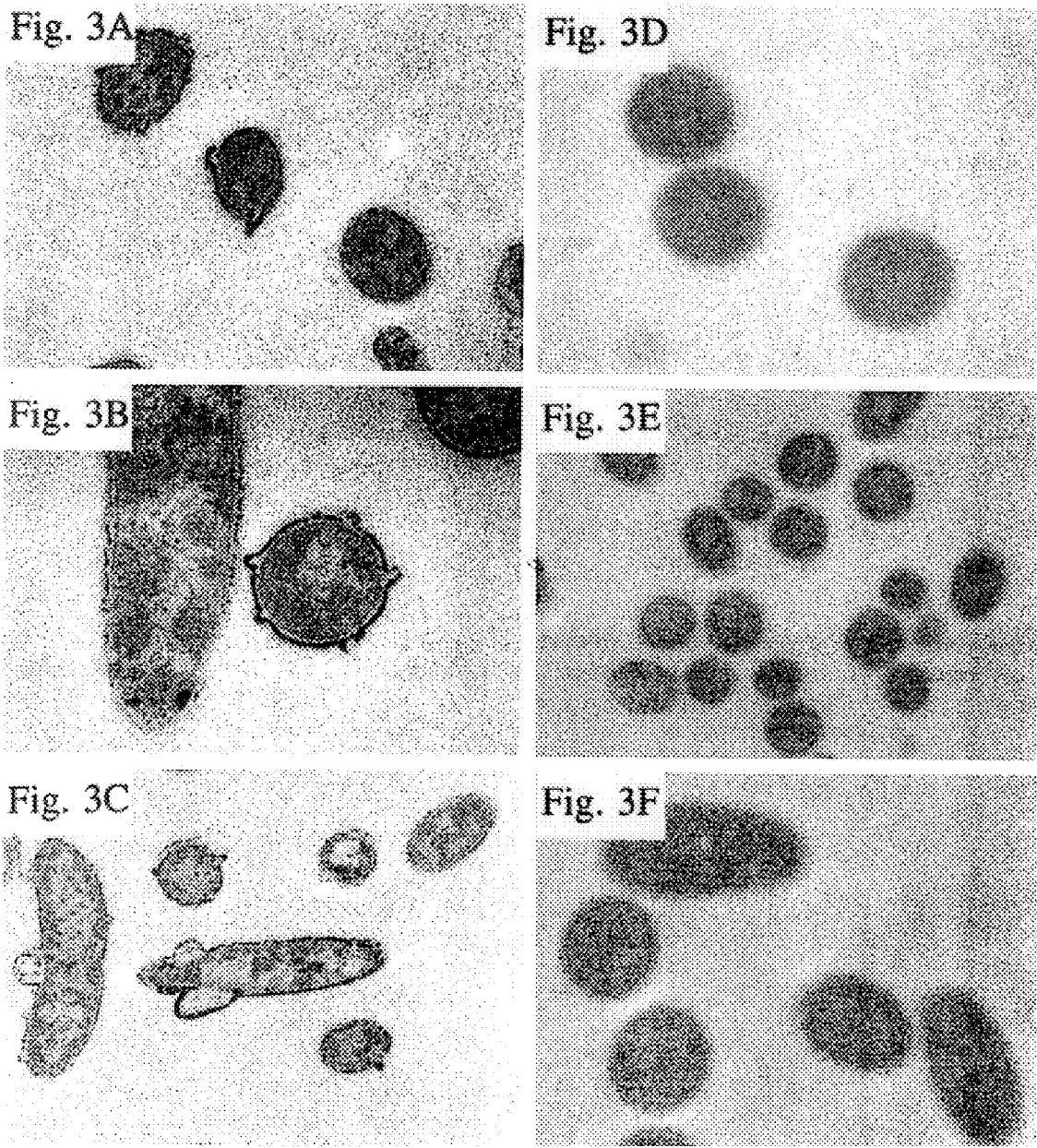
FIGS. 3A, 3B and C show transmission electron micrographs of cells from a mid-exponential phase culture of *S. ruminantium* JY35 incubated for reaction product deposition by phytase using sodium phytate as the substrate. Untreated control cells are shown for comparison in FIGS. 3D, 3E and 3F.

*S. ruminantium* JY35 (ATCC 55785) phytase activity was determined to be predominantly cell associated. Little phytase activity was detected in culture supernatants and cell washes. The phytase activity of *S. ruminantium* JY35 (ATCC 55785) was localized by electron microscopy as described by Cheng and Costerton (1973). Cells were harvested by centrifugation, washed with buffer, embedded in 4% (w/v) agar, prefixed in 0.5% glutaraldehyde solution for 30 min and fixed for 2 hours in 5% (v/v) glutaraldehyde solution. Samples were washed five times with cacodylate buffer (0.1 M, pH 7.2) and treated with 2% (w/v) osmium tetroxide, washed five times with cacodylate buffer, dehydrated in a graded ethanol series, and embedded in Spurr's resin (J. B. EM Services Inc.). Ultrathin sections were cut with a Reichert model OM U3 ultramicrotome and stained with 2% (w/v) uranyl acetate and lead citrate. Specimens were viewed with Hitachi H-500 TEM at an accelerating voltage of 75 kV. A comparison of *S. ruminantium* JY35 (ATCC 55785) cells incubated with substrate for reaction product deposition with untreated cells clearly indicated that the phytase activity was associated with the cell outer membrane surfaces (FIG. 3). Deposition of electron dense material on the outer cell surfaces of treated cells was the result of phytase activity (FIGS. 3A, B and C).

C. Phytase pH optimum

Figure 4:
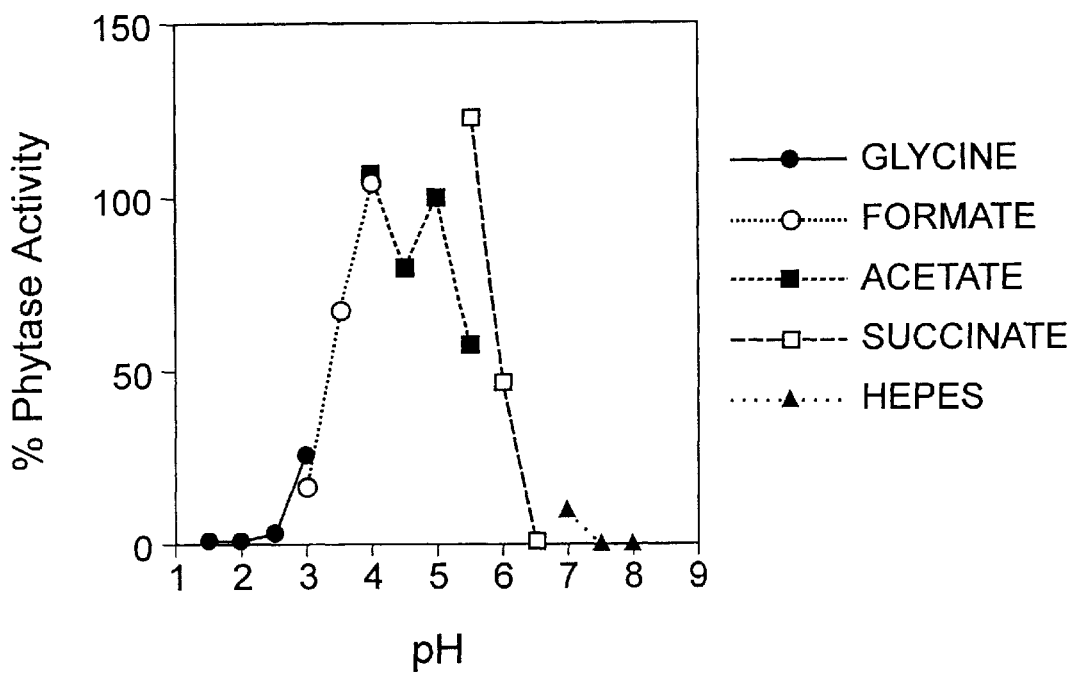
FIG. 4 is a graph illustrating the phytase pH profile for washed *S. ruminantium* JY35 cells in five different buffers.
Figure 5:
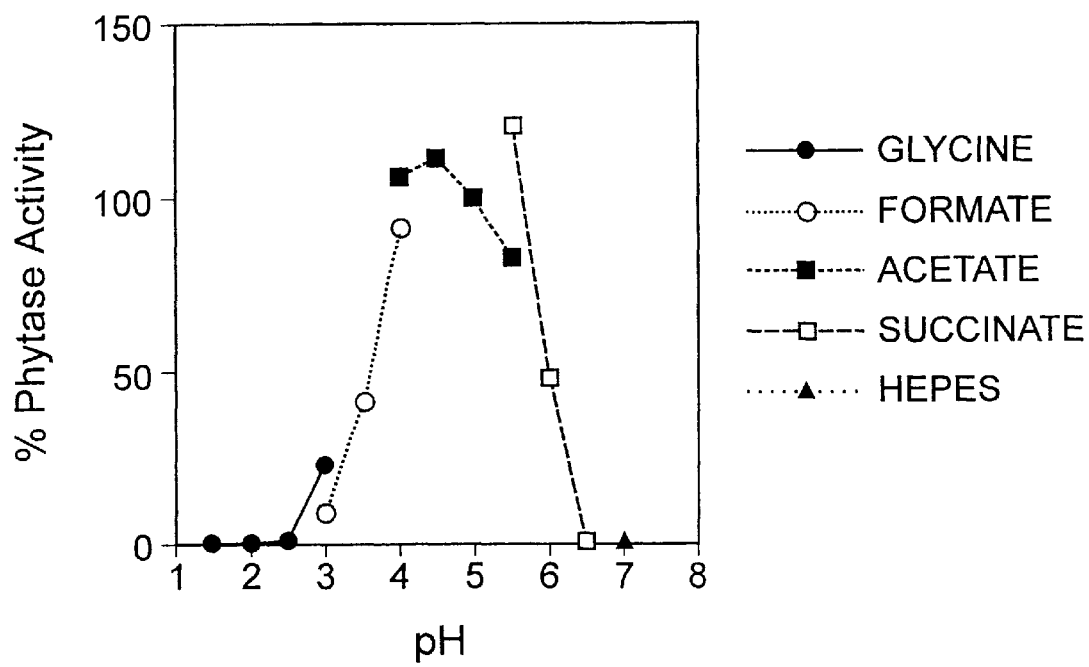
FIG. 5 is a graph illustrating the pH profile of *S. ruminantium* JY35 $MgCl_2$ cell extract in five different buffers.

Initial determinations of the pH optimum of the *S. ruminantium* JY35 (ATCC 55785) phytase were conducted with whole cells. Phytase activity was optimal over a pH range of 4.0 to 5.5 (FIG. 4). A second pH curve was generated with a $MgCl_2$ cell extract (FIG. 5). Cells from a 100-mL overnight culture were washed twice with sterile distilled water, resuspended in 0.3 volumes of a 0.2 M $MgCl_2$ aqueous solution and incubated overnight at 0° C. The solution was clarified by centrifugation and the resulting extract was used in phytase assays. Four buffers systems were used to cover the pH range; glycine (pH 1.5–3.0), formate (pH 3.0–4.0), acetate (pH 4.0–5.5) and succinate (pH 5.5–6.5).

D. Phytase temperature optimum

Figure 6:
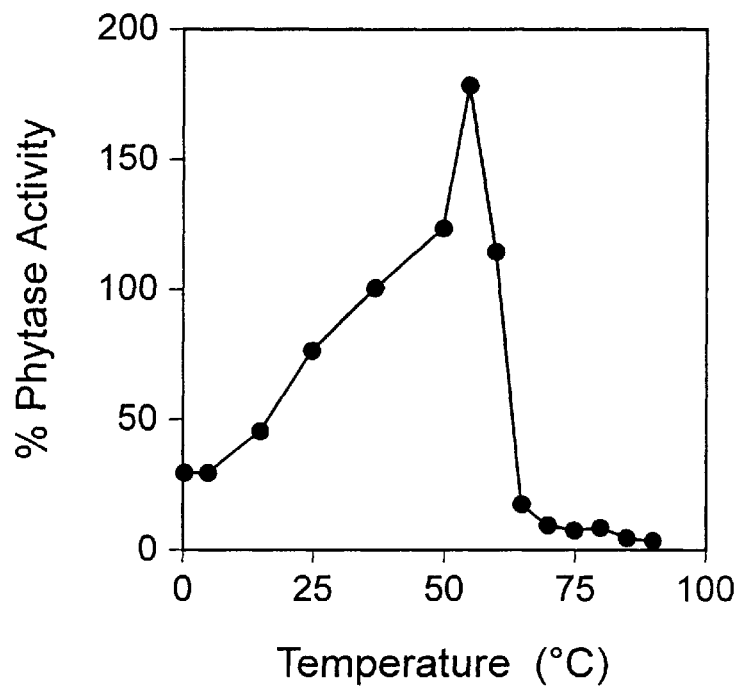
FIG. 6 is a graph illustrating the temperature profile of *S. ruminantium* JY35 $MgCl_2$ cell extract.

The temperature optimum of the *S. ruminantium* JY35 (ATCC 55785) phytase activity was determined at pH 5.0 (0.1 M sodium acetate buffer) with $MgCl_2$ cell extract. The enzyme retained over 50% of its activity over a temperature range of 37 to 55° C. (FIG. 6).

E. The effect of ions and substrate concentration on phytase activity

Figure 7:
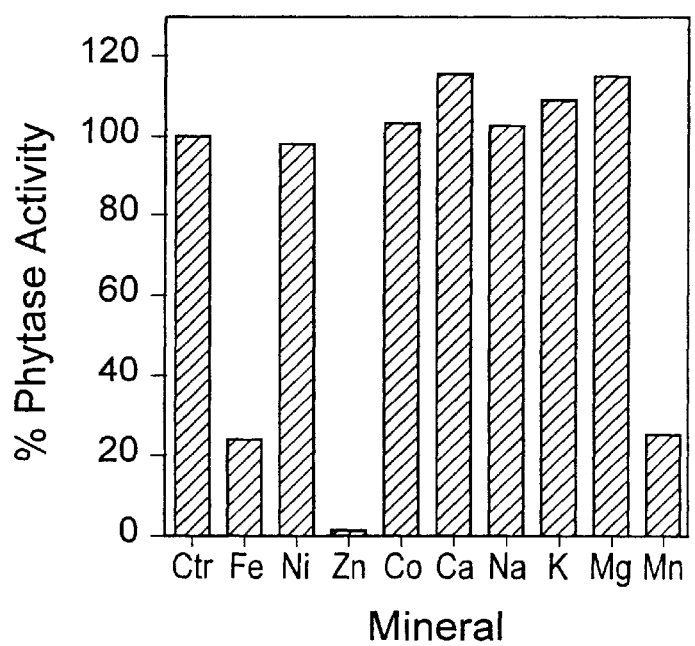
FIG. 7 is a graph illustrating the effect of ions (10 mM) on *S. ruminantium* JY35 phytase activity (Ctr=control).
Figure 8:
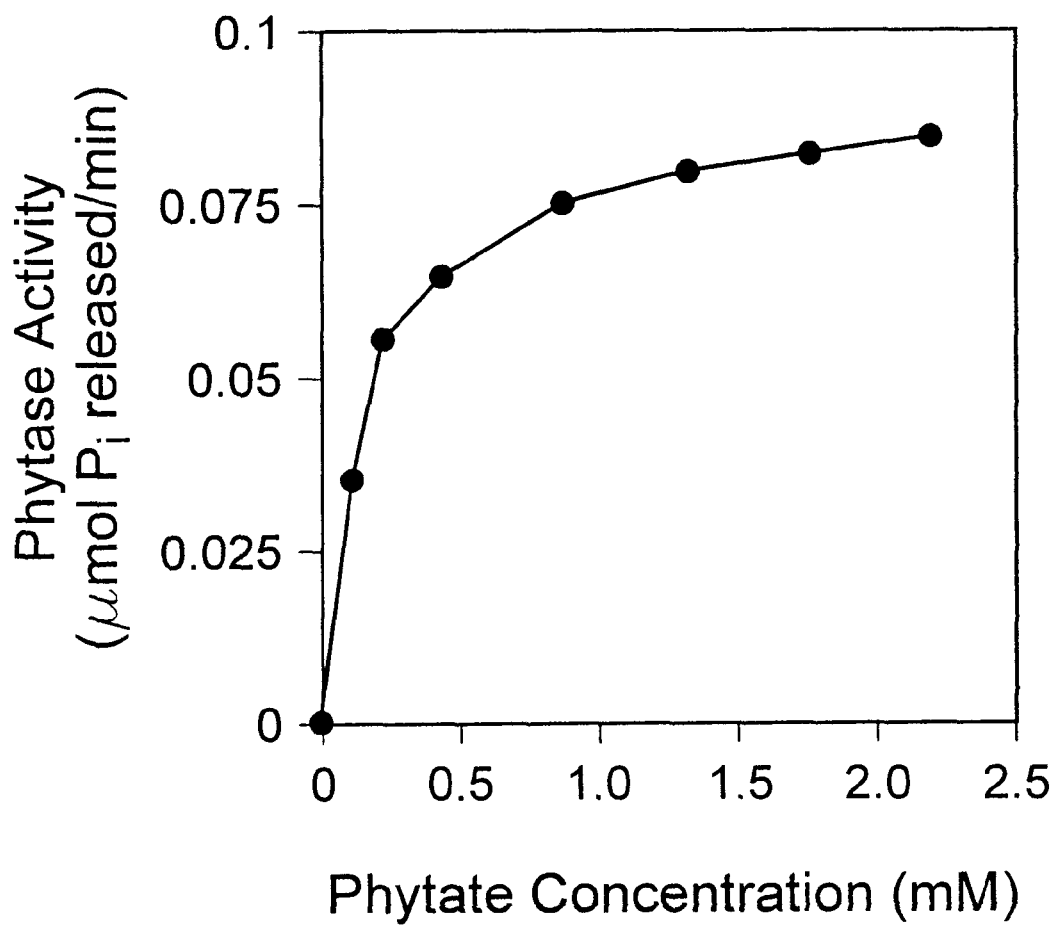
FIG. 8 is a graph illustrating the effect of sodium phytate concentration on *S. ruminantium* JY35 phytase activity.

The effect of various ions (10 mM) and substrate concentration on whole cell phytase activity were determined at pH 5.0 (0.1 M sodium acetate buffer). Phytase activity was stimulated by the addition of $Ca^{++}$, $Na^+$, $K^+$ and $Mg^{++}$, inhibited by $Fe^{++}$, $Zn^{++}$ and $Mn^{++}$ and unaffected by $Co^{++}$ and $Ni^{++}$ (FIG. 7). The effect of substrate concentration on phytase activity in a *S. ruminantium* JY35 (ATCC 55785) $MgCl_2$ cell extract is presented in FIG. 8.

F. Molecular Weight

Figure 9:
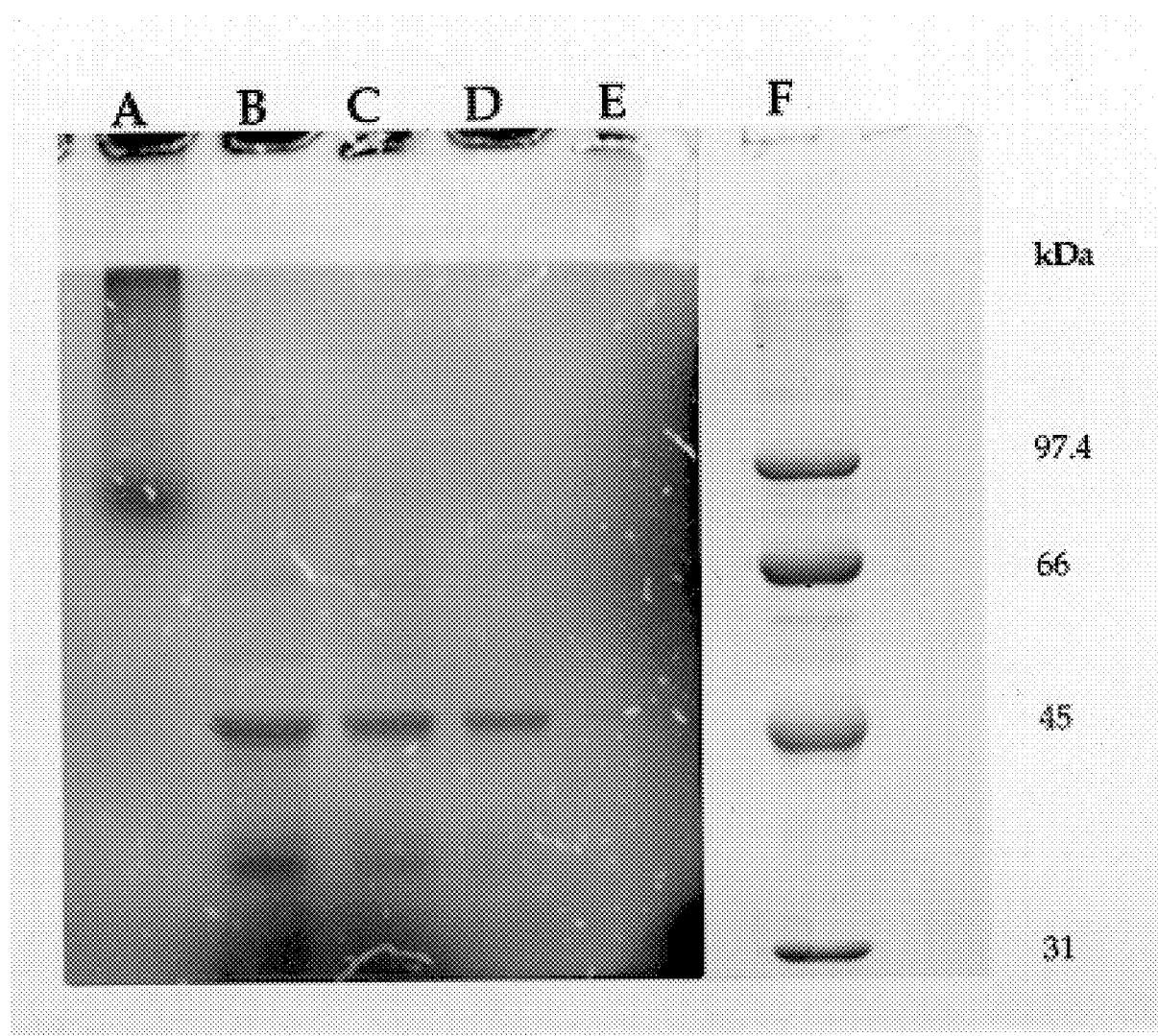
FIG. 9 is a zymogram developed for confirmation of phytase activity. Concentrates (10×) of *S. ruminantium* JY35 $MgCl_2$ extract (lanes B–E), low molecular weight markers (lane F, BioRad Laboratories Canada Ltd, Mississauga, Ontario) and *A. ficuum* phytase (Sigma, 1.6 U, lane A) were resolved by SDS-PAGE in a 10% polyacrylamide gel. Lanes A to E were stained for phytase activity and Lane F was stained with Coomassie brilliant blue.

The molecular size of the phytase in *S. ruminantium* JY35 (ATCC 55785) was determined by zymogram analysis. A ten-fold concentrated crude $MgCl_2$ released extract was mixed with 20 µL of sample loading buffer (Laemmli, 1970) in a microtube and the microtube was placed in a boiling water bath for 5 minutes. The denatured $MgCl_2$ extracts were resolved by SDS-PAGE on a 10% separating gel topped with a 4% stacking gel (Laemmli, 1970). Following electrophoresis, the phytase was renatured by soaking the gel in 1% Triton X-100 for 1 h at room temperature and 0.1 M sodium acetate buffer (pH 5.0) for 1 h at 4° C. Phytase activity was detected by incubating the gel for 16 h in a 0.1 M sodium acetate buffer (pH 5.0) containing 0.4% sodium phytate. The gel was treated with the cobalt chloride and ammonium molybdate/ammonium vanadate staining procedure described for the phytase plate assays in Example 2. A single dominant activity band, corresponding to a molecular mass of approximately 35 to 45 kDa, was observed (FIG. 9).

EXAMPLE 4

Cloning of a Phytase Gene (phyA) from *Selenomonas ruminantium* JY35 (ATCC 55785)

A. Isolation of phytase positive *Escherichia coli* clone

Figure 10:
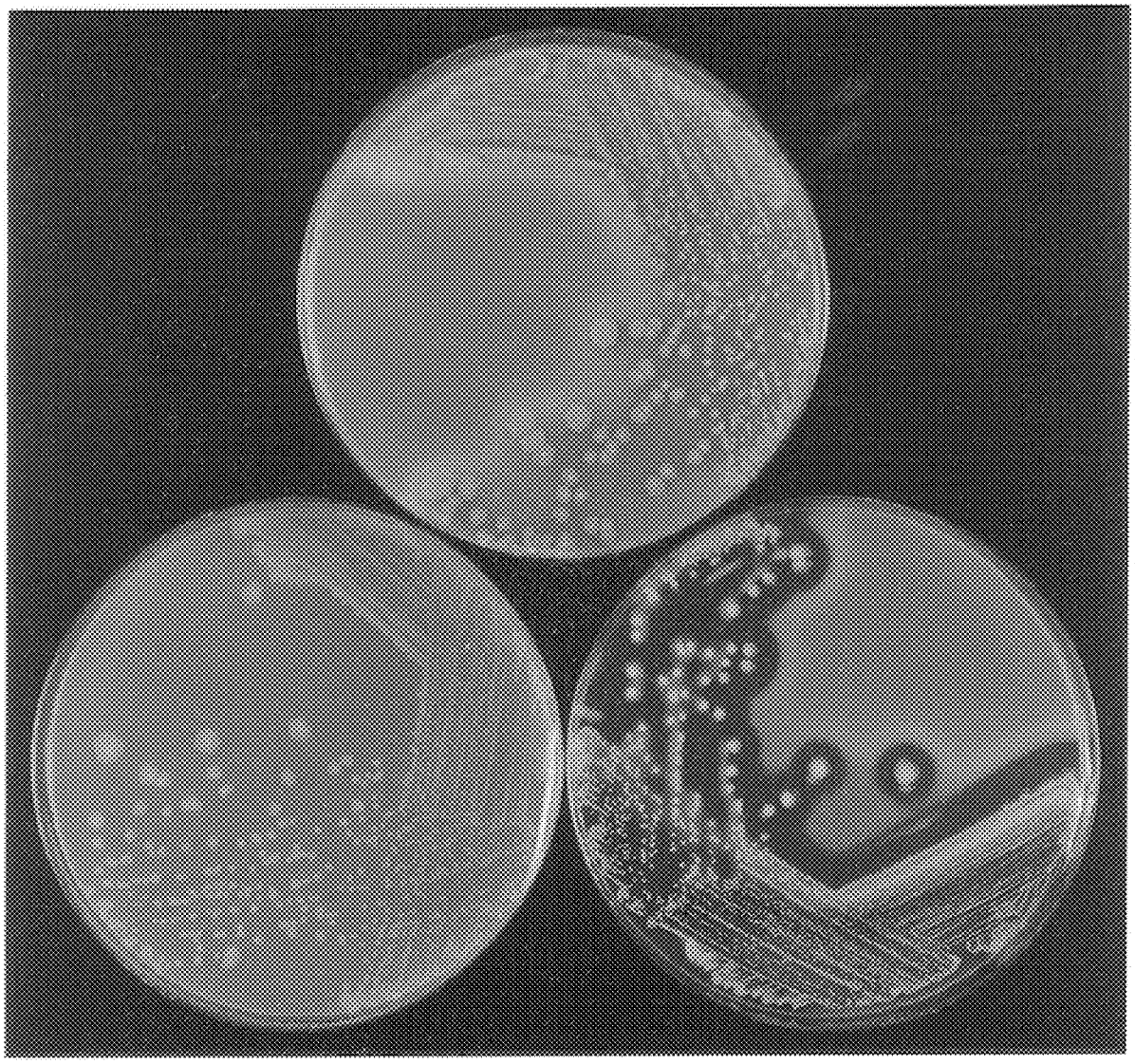
FIG. 10 is a photograph of a phytate hydrolysis plate assay for phytase activities of *E. coli* DH5α transformed with pSrP.2 (top), pSrP.2ΔSphl (bottom left), and pSrPf6 (bottom right). Zones of clearing were visible after incubating the plates at 37° C. for 48 h.

Genomic DNA libraries were prepared for *S. ruminantium* JY35 (ATCC 55785) according to published procedures (Hu et al., 1991; Sambrook et al., 1989). Genomic DNA was extracted from a fresh overnight culture of *S. ruminantium* JY35 (ATCC 55785) using a modification of the protocol described by Priefer et al. (1984). *S. ruminantium* JY35 (ATCC 55785) genomic DNA was partially digested with Sau3A and gel purified to produce DNA fragments in the 2- to 10-kb range. A genomic library was constructed by ligating BamHI-digested, dephosphorylated pUC18 with *S. ruminantium* JY35 (ATCC 55785) Sau3A genomic DNA fragments. *Escherichia coli* DH5α competent cells (Gibco BRL, Mississauga, ON) were transformed with the ligation mix and 6,000 clones carrying inserts were screened for phytase activity (zones of clearing) on LB phytase screening agar [LB medium, 1.0% sodium phytate (filter sterilized), 100 mM HEPES (pH 6.0–6.5), and 0.2% $CaCl_2$] containing ampicillin (100 µg/mL). A phytase-positive clone SrP.2 was isolated and phytase activity confirmed through enzyme assays (FIG. 10). Very high levels of phytase activity were found in the medium as well as associated with the *E. coli* cells (Table 3). Plasmid DNA isolated from clone SrP.2 carried a 5.5-kb plasmid, designated pSrP.2, consisting of pUC18 containing a 2.7-kb Sau3A insert.

B. Confirmation of the *Selenomonas ruminantium* JY35 (ATCC 55785) origin of the 2.7-kb insert The *S. ruminantium* JY35 (ATCC 55785) origin of the 2.7-kb insert in pSrP.2 was confirmed by Southern blot hybridization (Sambrook et al., 1989). Genomic DNA isolated from *S. ruminantium* JY35 (ATCC 55785) and digested with EcoRI or HindIII was resolved on a 0.8% agarose gel. After transfer to Zeta-probe® membrane (BioRad Laboratories), the hybridization was performed overnight at high stringency (2×SSC; 65° C.) with the 2.7-kb fragment from pSrP.2 labelled with digoxigenin (DIG DNA labeling and detection kit; Boehringer Mannheim Canada Ltd., Laval, PQ). The blots were washed twice in 2×SSC at room temperature; 0.1% SDS for 5 minutes and twice 0.1×SSC; 0.1% SDS for 20 minutes at 65° C. The blots were developed according to the protocol provided with the DIG DNA labeling and detection kit (Boehringer Mannheim Canada Ltd).

Figure 11:
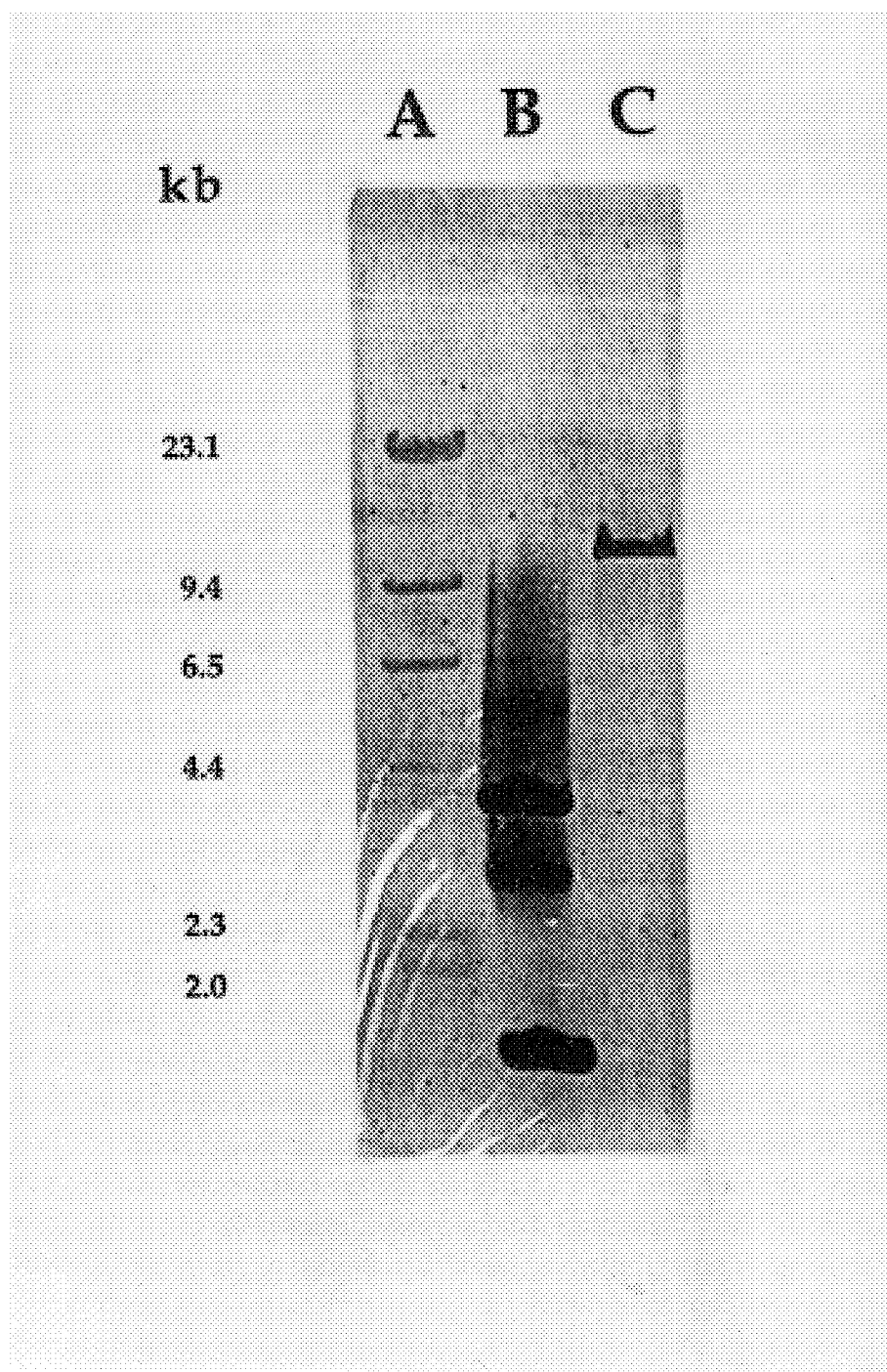
FIG. 11 is a Southern blot analysis using the 2.7-kb fragment from pSrP.2 as a probe against Sph1 digested pSrP.2 DNA (lane B) and HindIII digested genomic DNA isolated from *S. ruminantium* JY35 (lane C). Digoxigenin labelled HindIII digested Lambda DNA was run as a molecular weight standard in lane A.

The probe reacted with a 14-kb HindIII (FIG. 11) and a 23-kb EcoRI (data not shown) fragment of genomic DNA and confirmed that the 2.7-kb fragment was from *S. ruminantium* JY35 (ATCC 55785) and that a single homologous sequence exists in the genome. Single copies of a sequence homologous to the 2.7-kb fragment from *S. ruminantium* JY35 (ATCC 55785) also exist in the genomes of *S. ruminantium* HD86, HD141, and $HD_4$ (data not shown). However restriction fragment length polymorphisms were noted for *S. ruminantium* HD86 (9- and 23-kb EcoRI fragments) and *S. ruminantium* $HD_4$ (3-kb EcoRI fragment and a 20-kb HindIII fragment). The labelled 2.7-kb fragment from pSrP.2 failed to hybridize with genomic DNA isolated from *Prevotella* sp. 46/5[2], *E. coli* DH5α or *A. ficuum* NRRL 3135 (data not shown).

EXAMPLE 5
Characterization of *Selenomonas ruminantium* Phytase Gene

A. Evidence for the cloning of a phytase gene

*Escherichia coli* DH5α competent cells (Gibco BRL, Mississauga, ON) were transformed with plasmids pUC18 and pSrP.2. The resulting ampicillin-resistant transformants were tested for phytase activity on LB phytase screening agar. Only *E. coli* DH5α cells transformed with pSrP.2 produced clearing zones on LB phytase screening agar.

B. Restriction and deletion analysis of pSrP.2

Figure 12:
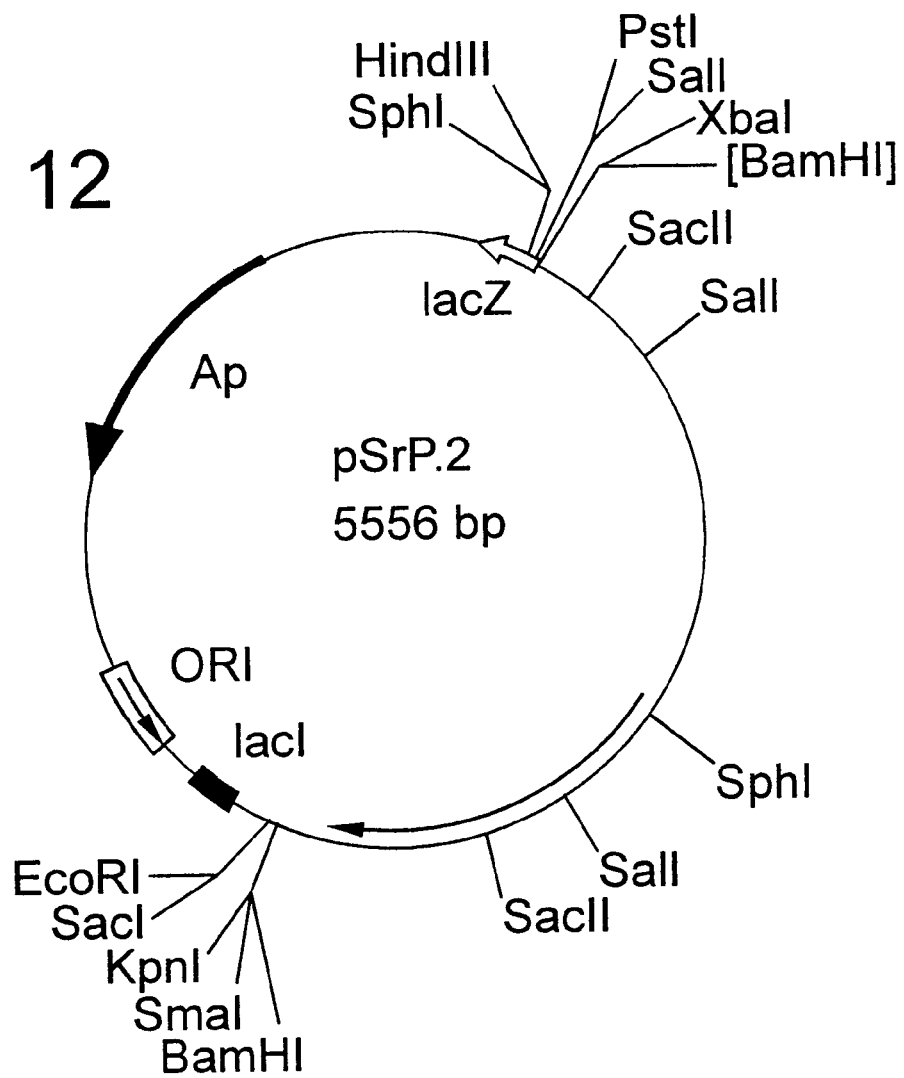
FIG. 12 is a physical map of pSrP.2. A 2.7-kb fragment, from a Sau3A partial digest of *S. ruminatium* JY35 genomic DNA, was cloned into the BamHI site of pUC18. This fragment contains the entire gene encoding the phytase from *S. ruminatium* JY35. The location of a BamHI site lost as a result of the ligation is indicated in square brackets.
Figure 13:
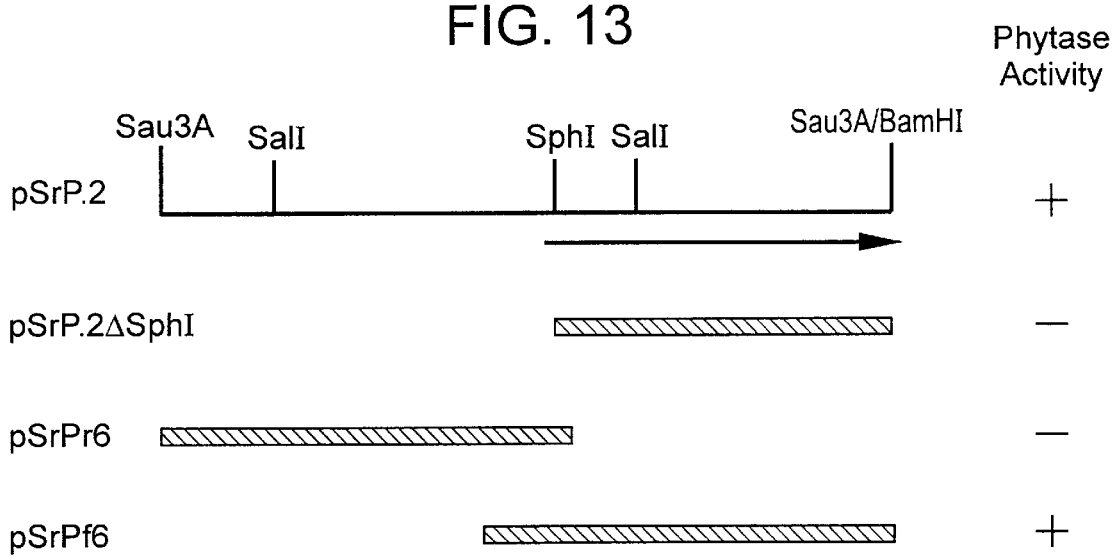
FIG. 13 is a schematic representation of the deletion analysis of the *S. ruminatium* phytase gene. The position of phyA is indicated by the horizontal arrow. The hatched boxes indicate segments of the 2.7-kb Sau3A fragment carried by different plasmid derivatives. Phytase activity is indicated in the panel to the right.

The phytase gene was localized on the 2.7-kb Sau3A insert by restriction endonuclease and deletion analyses (Ausubel et al., 1990; Sambrook et al., 1989). Cells carrying plasmid pSrP.2ΔSphl, constructed by the deletion of the 1.4-kb Sphl fragment from pSrP.2, lacked phytase activity (FIG. 12 and FIG. 13, Table 3).

C. Zymogram analysis

Figure 14:
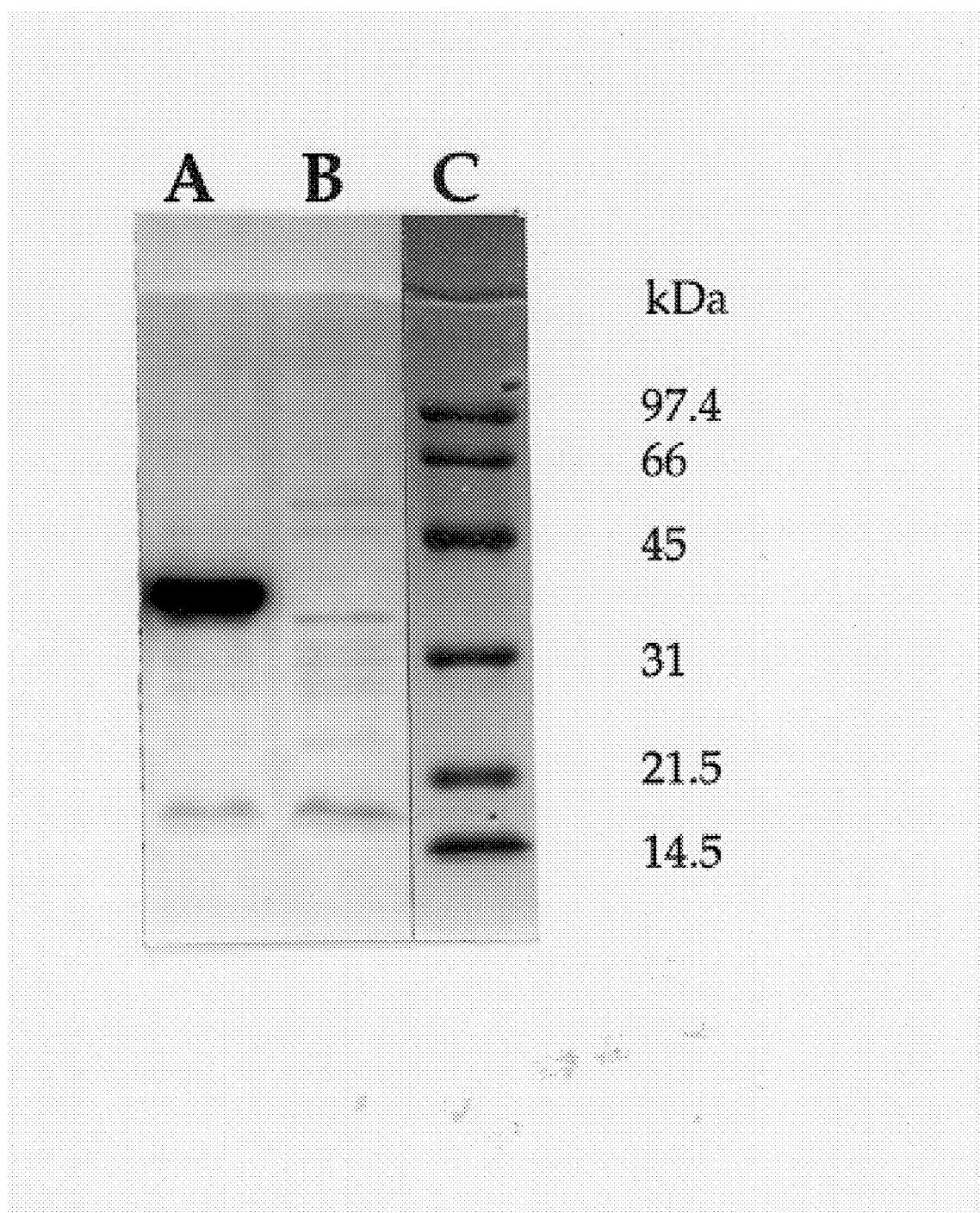
FIG. 14 is a zymogram developed for phytase activity. *E. coli* DH5α (pSrP.2) cells (lane A), *E. coli* DH5α (pSrP.2ΔSphl) cells (lane B), and low molecular weight markers (lane C, BioRad Laboratories) were resolved by SDS-PAGE in a 10% polyacrylamide gel. Lanes A and B were stained for phytase activity and Lane C was stained with Coomassie brilliant blue.

The molecular mass of the phytase produced by *E. coli* DH5α (pSrP.2) was determined by zymogram analysis. One mL of an overnight culture was transferred to a 1.5-mL microtube. The cells were harvested by centrifugation and washed with 0.1 M sodium acetate buffer (pH 5.5). The cell pellet was resuspended in 80 μL of sample loading buffer (Laemmli, 1970) and the microtube was placed in a boiling water bath for 5 minutes. The resulting cell extracts were resolved by SDS-PAGE on a 10% separating gel topped with a 4% stacking gel (Laemmli, 1970) and the gel was stained for phytase activity as described in Example 3F. A single dominant activity band, corresponding to a molecular mass of approximately 37 kDa, was observed (FIG. 14, lane A). A corresponding activity band was not observed for *E. coli* DH5α (pSrP.2ΔSphl) cells (FIG. 14, lane B).

D. DNA sequence analysis of pSrP.2

The complete sequence of the 2.7-kb insert of pSrP.2 was determined. Samples were prepared for DNA sequence analysis on an Applied Biosystems Model 373A DNA sequencing system (Applied Biosystems, Inc., Mississauga, ON) by using a Taq DyeDeoxy™ Terminator Cycle Sequencing Kit (Applied Biosystems, Inc.). Template DNA was extracted from overnight cultures of *E. coli* DH5α (pSrp.2) with the Wizards™ minipreps DNA purification system (Promega Corp., Madison, Wis.). Overlapping sequences were generated by primer walking. The DNA sequence data was analyzed using MacDNASIS DNA software (Hitachi Software Engineering Co., Ltd., San Bruno, Calif.).

The sequence of the 2.7-kb DNA insert was determined and DNA structural analysis identified an open reading frame (ORF2; bp 1493 to 2504) overlapping the Sphl site of the 2.7-kb Sau3A insert and large enough to encode the 37 kDa phytase. Phytase activity was eliminated by deleting bp 1518 through to the end of the 2.7-kb Sau3A fragment (pSrPr6, Table 3, FIG. 13). This was accomplished by cloning the PCR product of pSrP.2 bounded by sequencing primer SrPr6 (CGG GAT GCT TCT GCC AGT AT, SEQ ID NO. 3 the reverse complement of bp 1518 to 1538) and M13 Forward primer (CGC CAG GGT TTT CCC AGT CAC GAC) into pGEM-T (Promega Corp.). A PCR product subclone (pSrPf6) of pSrP.2, bounded by primer SrPf6 (bp 1232 to 1252, CGT CCA CGG AGT CAC CCT AC) SEQ ID NO. 4 and M13 Reverse primer (AGC GGA TAA CAA TTT CAC ACA GGA), and containing ORF2 plus 252 bp upstream of the Sphl cleavage site retained phytase activity (Table 3, FIG. 13).

The sequence and translation of the *S. ruminatium* phytase gene (phyA) is shown in FIG. 15. Translation of ORF2 would result in the expression of a 346-amino acid polypeptide with a predicted molecular weight of 39.6 kDa (FIG. 15). The first 31 residues were typical of a prokaryote signal sequence, encompassing a basic N-terminus and central hydrophobic core (von Heijne, 1986). Application of the method of von Heijne (1986) predicted the signal peptidase cleavage site most probably occurs before Ala$^{28}$ or Pro$^{31}$. This was confirmed by determining the N-terminal amino acid sequence of gel purified from *E. coli* DH5α (pSrPf6) culture supernatant (FIG. 15). The secreted mature protein has a putative mass of 36.5 kDa.

A comparison of the phyA amino acid sequence with known protein sequences from the MasDNASIS SWIS-SPROT database revealed no significant similarities to any published sequences including *Aspergillus niger* phytase genes phyA and phyB.

EXAMPLE 6
Partial Purification and Characterization of phyA Products Expressed by *E. coli*.

Cell free supernatants, prepared from overnight cultures of *E. coli* (pSrPf6), were mixed 3:1 (v/v) with Ni$^{++}$-NTA agarose pre-equilibrated in 0.1 M Tris (pH 7.9), 0.3 M NaCl buffer. The mixture was incubated at room temperature for 0.5 h and washed 3× with 0.1 M Tris (pH 7.9), 0.3 M NaCl buffer. The phytase activity was eluted from the resin with 1 volume 0.1 M sodium acetate (pH 5.0), 0.3 M NaCl. When resolved on SDS-polyacrylamide gels stained with Coomassie brilliant blue, over 70% of the eluted protein formed a single 37-kDa protein band. Zymogram and N-terminal amino acid sequence analyses confirmed that the 37-kDa band corresponded to the phytase encoded by the cloned *S. ruminantium* JY35 (ATCC 55785) phyA. The specific activity of Ni$^{++}$-NTA agarose-purified phytase ranged from 200 to 400 μmol phosphate released/min/mg protein. This is 2 to 4 times higher than the specific activity reported for the purified *A. ficuum* NRRL 3135 phytase (van Gorcum et al., 1991, 1995; van Hartingsveldt et al., 1993).

EXAMPLE 7
Overexpression of the *Selenomonas ruminatium* phyA gene

Isolation and characterization of phyA from *S. ruminantium* JY35 (ATCC 55785) enables the large scale production of protein PhyA in any of a number of prokaryotic (e.g., *E. coli* and *B. subtilis*) or eukaryotic (e.g., fungal—Pichia, Saccharomyces, Aspergillus, Trichoderma; plant—Brassica, Zea, Solanum; or animal—poultry, swine or fish) expression systems using known methods. Teachings for the construction and expression of phyA in *E. coli*, *P. pastoris*, and *B. napus* are provided below. Similar approaches may be adopted for expression of the *S. ruminantium* JY35 (ATCC 55785) phytase in other prokaryotic and eukaryotic organisms.

A. Cloning of the *Selenomonas ruminatium* phyA in an *Escherichia coli*—specific expression construct An expression construct is constructed in which the region encoding the mature PhyA is transcriptionally fused with the tac promoter (Brosius et al., 1985). The promoter sequences may be replaced by those from other promoters that provide for efficient expression in *E. coli*. The expression construct is introduced into *E. coli* cells by transformation.

i. Construction of the *E. coli* expression vector

A number of *E. coli* expression vectors based on the tac or related promoters are commercially available. In this example the construct will be prepared with pKK223-3 available from Pharmacia Biotech Inc. (Uppsala, Sweden). The region of phyA encoding the mature PhyA (the peptide secreted following removal of the signal peptide) is amplified with oligonucleotide primers MATE2 (GC GAA TTC ATG GCC AAG GCG CCG GAG CAG AC) (SEQ ID NO. 5) and M13 Reverse. The oligonucleotide MATE2 (SEQ ID NO.5) was designed to contain a suitable restriction site at its terminus to allow direct assembly of the amplified product with pKK223-3. The region of phyA amplified with MATE2 (SEQ ID NO. 5) and M13 Reverse is digested with EcoRI and SmaI and ligated into similarly cleaved pKK223-3.

ii. Transformation of E. coli and PhyA expression

The pKK223-3::phyA ligation mix is used to transform competent E. coli cells. Strains suitable for high levels of protein expression, such as SG13009, CAG926 or CAG929 (carrying lacI on a plasmid such as pREP4), are employed. Transformed cells are spread on LB agar containing ampicillin (100 μg/mL) and incubated overnight at 37° C. Ampicillin-resistant colonies are screened for the presence of the desired pKK223-3::phyA construct by extracting pDNA and subjecting the pDNA to agarose gel electrophoresis and restriction analysis. Positive clones may be further characterized by PCR and DNA sequence analysis.

Expression of the S. ruminantium JY35 (ATCC 55785) phytase by transformed E. coli cells is tested by growing the cells under vigorous aeration at 37° C. in a suitable liquid medium (e.g., LB or 2xYT) containing the appropriate antibiotic selection until the optical density (at 600 nm) is between 0.5 and 1.0. The tac promoter is induced by adding isopropyl-β-D-thiogalactoside (IPTG) to a final concentration between 0.1 and 2 mM. The cells are cultivated for an additional 2 to 4 h and harvested by centrifugation. Protein expression is monitored by SDS-PAGE, and western blot/immunodetection techniques. The expressed PhyA may be extracted by breaking (e.g., sonication or mechanical disruption) the *E. coli* cells. Protein inclusions of PhyA may be harvested by centrifugation and solubilized with 1 to 2% SDS. The SDS may be removed by dialysis, electroelution or ultrafiltration. The phytase activity of prepared cell extracts may be assayed by standard methods described in Example 2.

B. Cloning of the *Selenomonas ruminatium* phyA in a *Pichia pastoris*—specific expression construct An expression construct is constructed in which the region encoding the mature PhyA is translationally fused with the secretion signal sequences found on *P. pastoris* expression vectors (Pichia Expression Kit Instruction Manual, Invitrogen Corporation, San Diego, Calif.) in order to express the *S. ruminantium* phytase as a secreted product. The promoter and secretion signal sequences may be replaced by those from other promoters that provide for efficient expression in Pichia. The expression construct is introduced into *P. pastoris* cells by transformation.

i. Construction of the *P. pastoris* expression vector

A number of *P. pastoris* expression vectors based on the aox1 promoters and α-Factor or pho1 signal sequences are commercially available. In this example the construct will be prepared with pPIC9 available from Invitrogen Corporation. The region of phyA encoding the mature PhyA is amplified with oligonucleotide primers MATE (GC GAA TTC GCC AAG GCG CCG GAG CAG AC) (SEQ ID NO. 6) and M13 Reverse. The oligo MATE (SEQ ID NO. 6) was designed to contain a suitable restriction site at its terminus to allow direct assembly of the amplified product with pPIC9. The region of phyA amplified with MATE (SEQ ID NO. 6) and M13 Reverse is digested with EcoRI and ligated into similarly cleaved pPIC9.

ii. Transformation of *P. pastoris* and PhyA expression

The pPIC9::phyA ligation mix is used to transform competent *E. coli* DH5α cells. Transformed cells are spread on LB agar containing ampicillin (100 $\mu$g/mL) and incubated overnight at 37° C. Ampicillin-resistant colonies are screened for the presence of the desired pPIC9::phyA construct by extracting pDNA and subjecting the pDNA to agarose gel electrophoresis and restriction analysis. Positive clones are further characterized by PCR and DNA sequence analysis. Plasmid DNA is prepared from a 1 L culture of an *E. coli* clone carrying the desired pPIC9::phyA construct. The pDNA is digested with Bg/II and analyzed by agarose gel electrophoresis to confirm complete digestion of the vector. The digested pDNA is extracted with phenol:chloroform, ethanol precipitated and resuspended in sterile distilled $H_2O$ to a final concentration of 1 $\mu$g/mL. In preparation for transformation, *P. pastoris* GS115 or KM71 cells are grown for 24 h at 30° C. in YPD broth. Cells from 100 $\mu$L of culture are harvested by centrifugation and resuspended in 100 $\mu$L of transformation buffer (0.1 M LiCl, 0.1 M dithiothreitol, 45% polyethylene glycol 4000) containing 10 $\mu$g salmon sperm DNA and 10 $\mu$g of linearized pPIC9::phyA. The mixture is incubated for 1 h at 37° C., spread on *P. pastoris* minimal agar medium and incubated for 2 to 5 d. Colonies growing on the minimal agar medium are streaked for purity and analyzed for the presence of the integrated phyA by PCR and Southern blot hybridization.

Expression of the *S. ruminantium* JY35 (ATCC 55785) phytase by transformed *P. pastoris* cells is tested by growing the cells at 30° C. under vigorous aeration in a suitable liquid medium (e.g. buffered complex glycerol medium such as BMGY) until a culture optical density (at 600 nm) ($OD_{600}$) of 2 to 6 is reached. The cells are harvested and resuspended to an $OD_{600}$ of 1.0 in an inducing medium (e.g., buffered complex methanol medium, BMMY) and incubated for a further 3 to 5 days. Cells and cell-free culture supernatant are collected and protein expression is monitored by enzyme assay, SDS-PAGE, and western blot/immunodetection techniques.

C. Cloning of the *Selenomonas ruminatium* phyA in a *Pichia pastoris*—specific expression construct—A Further Example An expression construct is constructed in which the region encoding the mature PhyA is translationally fused with the secretion signal sequences found on *P. pastoris* expression vectors (e.g., Pichia Expression Kit Instruction Manual, Invitrogen Corporation, San Diego, Calif.) in order to express the *S. ruminantium* phytase as a secreted product. The promoter and secretion signal sequences may be replaced by those from other promoters that provide for efficient expression in Pichia. The expression construct is introduced into *P. pastoris* cells by transformation.

i. Construction of the *P. pastoris* expression vector

A number of *P. pastoris* expression vectors based on the aox1 promoters and α-Factor or pho1 signal sequences are commercially available. In this example the construct was prepared with pPICZαA available from Invitrogen Corporation. The region of phyA encoding the mature PhyA (i.e., the peptide secreted following removal of the signal peptide) was amplified with oligonucleotide primers MATE (GC GAA TTC GCC AAG GCG CCG GAG CAG AC SEQ ID NO. 6) and M13 Reverse. The oligo MATE (SEQ ID NO. 6) was designed to contain an EcoRI restriction site at its terminus to allow direct assembly of the amplified product with pPICZαA. The region of phyA amplified with MATE (SEQ ID NO.6) and M13 Reverse was digested with EcoRI and ligated into similarly cleaved pPICZαA.

ii. Transformation of *P. pastoris*

The pPICZαA::phyA ligation mix was used to transform competent *E. coli* DH5α cells. Transformed cells were spread on LB agar containing Zeocin (25 mg/mL) and incubated overnight at 37° C. Zeocin resistant colonies were screened for the presence of the desired pPICZαA::phyA construct by extracting pDNA and subjecting the pDNA to agarose gel electrophoresis and restriction analysis. Positive clones were further characterized by PCR and DNA sequence analysis. Plasmid DNA was prepared from a 1 L culture of an *E. coli* clone carrying the desired pPICZαA::phyA construct. The pDNA is digested with Bg/II and analyzed by agarose gel electrophoresis to confirm complete digestion of the vector. The digested pDNA was extracted with phenol:chloroform, ethanol precipitated and resuspended in sterile distilled $H_2O$ to a final concentration of 1 μg/μL.

In preparation for transformation, 50 mL of YPD broth were inoculated with *P. pastoris* GS115 cells and incubated at 28° C. and 250 RPM for 1 day. Subsequently, 5 mL of the 1 d culture was used to inoculate 50 mL of fresh YPD broth. The culture was propagated overnight at 28° C. and 250 RPM. The following morning, 5 mL of this culture was used to inoculate 50 mL of fresh YPD broth. This culture was incubated at 28° C. and 250 RPM until the culture $OD_{600}$ reached approximately 1.2 (~6 h). The yeast cells from 20 ml of fresh culture were harvest by centrifugation, washed once with and resuspended in 1 mL of room temperature 10 mM Tris, 1 mM EDTA, 0.1 M LiCl, 0.1 M dithiothreitol buffer (pH 7.4). After a 1 h incubation at 30° C., the cell suspension was washed once with 1 mL ice cold water and once with 1 mL ice cold 1 M sorbitol. The cells were resuspended in 160 μL of ice cold 1 M sorbitol (to obtain cell concentrations approaching $10^{10}$ cells/mL). Linearized pPICZαA::phyA (5 to 10 μg) was mixed with 80 μL of cells, loaded into prechilled electroporation cuvettes (0.2 cm interelectrode distance) and incubated on ice for 5 min. A high voltage pulse (1.5 kV, 25 pF, 200 Ohms) was applied to the cuvette with a Bio-Rad Gene Pulser™. Immediately following the pulse, 1 mL of ice cold 1 M sorbitol was added to the cuvette which was incubated subsequently for 2 h at 30° C. The cell suspension was spread (100 to 200 μL per plate) on YPD agar medium containing Zeocin (100 μg/mL) and incubated for 2 to 4 d at 30° C. Colonies growing on the selective medium were streaked for purity and analyzed for the presence of the integrated phyA by PCR and/or Southern blot hybridization.

iii. *Pichia pastoris* expression of the *S. ruminantium* JY35 phytase gene

Expression of the *S. ruminantium* JY35 phytase by transformed *P. pastoris* cells was tested by growing transformed cells grown overnight in buffered complex glycerol medium (e.g., buffered complex glycerol medium, BMGY, Pichia Expression Kit Instruction Manual) at 28° C. and 250 RPM and transferring them into inducing medium (e.g., buffered complex methanol medium, BMMY). The cells harvested from the BMGY medium were washed once with BMMY medium, resuspended in BMMY to an $OD_{600}$ of 1.0 and incubated for a further 3 to 5 days at 28° C. and 250 RPM. Methanol (0.005 volumes) was added every 24 h. Cells and cell free culture supernatants were collected and assayed for phytase activity.

Sixteen *P. pastoris* pPICZαA::MATE transformants were tested for phytase activity following 96 h growth in BMMY medium. The most active transformant, named clone 17, was selected for further study. Growth and phytase production by *P. pastoris* pPICZαA::MATE clone 17 and a negative clone (*P. pastoris* pPICZαA) were monitored over a period of 9 d. Starter cultures were prepared by growing the isolates overnight (28° C., 250 RPM) in 10 mL of BMGY (glycerol) medium. The cells were harvested and duplicate cultures were prepared by resuspending the cells in 50 mL BMMY (methanol) medium to an approximate $OD_{600}$ of 2.5. The resulting cultures were transferred into 500 mL flasks and incubated at 28° C. and 250 RPM. Methanol was added every 24 h to a final concentration of 0.5%. Optical density and phytase activity were measured over the time course of the experiment. The results are presented in Table 4. Phytase activity was detected only in cultures carrying the *S. ruminantium* phyA gene. These cultures produced up to 22.5 units of phytase activity per mL after 210.5 h cultivation.

Phytase activity in shake flask cultures was increased through modification of the induction protocol and medium composition. The phytase activity of clone 17 was dramatically improved by increasing the initial cell density ($OD_{610}$=36.0) of the induced culture. After nearly 4 d growth (91.5 h), phytase activities greater than 40 and 20 units/mL were observed for whole culture and cell free supernatant samples, respectively. The optical densities ($OD_{610}$) of these cultures were between 62 and 69. Experimental results suggest that the greater the culture biomass at the time of methanol induction, the greater the yields of recombinant phytase. Biomass yields as high as 150 g/L (dry weight) or optical densities of 1500 have been reported for Pichia cultivated under optimal growth conditions in a tightly controlled fermentor system operating with oxygen enrichment.

Pichia phytase yields were also increased by adding Tween-80 to the medium. Surfactants have been shown previously to affect phytase production by *Aspergillus carbonarius* (Al-Asheh and Duvnjak, 1994). The effect of incorporating 0, 0.02, 0.1 or 0.5% Tween-80 on phytase yields of BMMY cultures of *P. pastoris* pPICZαA::MATE clone 17 is illustrated in Table 5. The cells from 2 d YPD cultures were harvested and resuspended in BMMY ($OD_{610}$=8.3). Triplicate flasks for each concentration of Tween-80 were prepared and incubated at 28° C. and 250 RPM. Methanol (0.005 volumes) was added on a daily basis to the flasks. Phytase activity increased more rapidly in cultures containing higher concentrations of Tween-80. Furthermore, a larger proportion of the phytase activity was found in the supernatant when higher Tween-80 concentrations were used. Phytase yields as high as 298 units/mL of shake flask culture have been achieved with a 9 d culture of clone 17 cultivated in BMMY medium amended with 0.5% Tween-80.

Cellular and supernatant proteins were analyzed by SDS-PAGE to confirm the production of PhyA by *P. pastoris*. The presence of a 37 kDa protein band was readily apparent when as little as 5 μL of supernatant was resolved on a 12% SDS-PAGE gel. The 37 kDa band was visible in the cellular protein sample but represented less than 10% of that found in the corresponding amount of supernatant. In addition to PhyA, supernatants from clone 17 contained very few additional proteins (a useful characteristic of Pichia expression). The recombinant PhyA protein comprised over 95% (estimated from SDS-PAGE gels) of the secreted protein. The 37 kDa protein band was not present in the supernatant or cells of a negative control culture (*P. pastoris* pPICZαA).

Shake flask experiments with recombinant *P. pastoris* cells expressing the *S. ruminantium* phytase (PhyA) have demonstrated the potential of this protein production system. Significant gains in phytase yields will be obtained by cultivating and inducing clone 17 in a fermentor. Additional gains in phytase yields may be achieved by increasing gene copy number through further screening of independent transformants or the use of multicopy vector systems. Spontaneous multiple plasmid integration events occur in Pichia at a frequency between 1/10 and 1/100 transformants. It is not unrealistic to expect that a 10 fold gain in phytase yield (e.g., 3,000 units/mL) may be readily achieved through manipulation of phytase gene copy number and control of fermentation parameters. This would result in production levels comparable to commercial *A. ficuum* phytase production systems. Yields for these systems are believed to be around 3,000,000 units (μmol Pi released/min) of phytase activity per L of culture.

iv. The Activity of recombinant the *S. ruminantium* phytase (PhyA) on grain substrates The liberation of phosphate from corn by the recombinant *S. ruminantium* JY35 phytase produced by *Pichia pastoris* was examined. Feed corn was ground and sieved through a mesh to obtain a particle size between 1–3 mm. Ground corn (0.5 g) was weighed into sterile 15 mL Falcon tubes to which 2 mL of 0.1 M sodium acetate buffer (pH 5.0) was added. After addition of phytase, the reaction mixtures were incubated at 37° C. Phosphate release was determined by measuring supernatant phosphate. In order to measure the background phosphate, reaction mixtures were prepared and terminated immediately through the addition of 5% (w/v) TCA. All experiments were conducted in triplicate.

Incubation of corn in a sodium acetate buffer resulted in the release of increasing amounts of phosphorus over time (Table 6). Although the addition of phytase activity significantly increased the amount of phosphorus released, the rate of phosphorus release decreased with time.

The concentration of phytase added to the incubation mixture also influenced the amount of phosphorus released. Raising phytase concentrations from 0.08 units to 0.48 units per g of corn resulted in increased levels of phosphorus in the supernatant (Table 7). It should be noted that increasing the phytase concentration from 0.32 to 0.48 units produced only a marginal increase in phosphorus released.

D. Cloning of the *Selenomonas ruminatium* phyA in a *Brassica napus* seed—specific expression construct Transformation and gene expression methods have been developed for a wide variety of monocotyledonous and dicotyledonous crop species. In this example, a *S. ruminantium* JY35 (ATCC 55785) phytase expression construct is constructed in which the region encoding the mature PhyA is translationally fused with an oleosin coding sequence in order to target seed oil body specific expression of the *S. ruminantium* phytase. The promoter and/or secretion signal sequences may be replaced by those from other promoters that provide for efficient expression in *B. napus* or other transformable plant species. The expression construct is introduced into *B. napus* cells by Agrobacterium-mediated transformation.

i. Construction of the *B. napus* expression vector

A number of expression vectors functional in *B. napus* are described in the literature (Gelvin et al., 1993). In this example, the construct is prepared by replacing the *E. coli* β-glucuronidase CDS of pCGOBPGUS (van Rooijen and Moloney, 1994) with a fragment encoding the phyA mature CDS. This is accomplished by subcloning the PCGOBPGUS PstI KpnI fragment, containing the oleosin promoter::oleosin CDS::β-glucuronidase CDS::NOS region, on to PstI KpnI-digested pUCBM20 (Boehringer Mannheim Canada, Laval, PQ). This plasmid is called pBMOBPGUS. The region of phyA encoding the mature PhyA is amplified with oligonucleotide primers MATN (GA GGA TCC ATG GCC AAG GCG CCG GAG CAG AC) (SEQ ID NO. 7) and M13 Reverse. The oligonucleotide MATN (SEQ ID NO. 7) was designed to contain a suitable restriction site at its terminus to allow direct assembly of the amplified product with digested pBMOBPGUS. The phyA fragment amplified with MATN (SEQ ID NO. 7) and M13 Reverse is digested with NcoI SstI and ligated into similarly cleaved pBMOBPGUS to generate plasmid pBMOBP phyA. The *B. napus* expression vector, pCGOBP phyA, is constructed by replacing the PstI KpnI fragment from pCGOBPGUS with the PstI KpnI fragment from pBMOBP phyA, containing the oleosin promoter::oleosin CDS::phyA CDS::NOS fragment.

ii. Transformation of *B. napus* and stable PhyA expression

Transgenic *B. napus* is prepared as described by van Rooijen and Moloney (1994). *Agrobacterium tumefaciens* strain EHA101 is transformed by electroporation with pCGOBP phyA. Cotyledonary petioles of *B. napus* are transformed with *A. tumefaciens* EHA101 (pCGOBP phyA). Transgenic plants are regenerated from explants that root on hormone-free MS medium containing 20 μg/mL kanamycin. Young plants are assayed for NPTII activity, grown to maturity and allowed to self pollenate and set seed. Seeds from individual transformants are pooled and part of the seed sample is assayed for the presence of phytase activity and compared to seeds from untransformed plants. Second generation plants (T2) are propagated from the seeds of clones with the highest levels of phytase activity. Seeds from the T2 plants homozygous for NPTII (hence also for phyA) are selected and used for mass propagation of plants (T3) capable of producing the highest amounts of phytase.

EXAMPLE 8

Identification of Related Phytase Genes in Other Microorganisms

To identify a phytase gene related to phyA, hybridization analysis can be used to screen nucleic acids from one or more ruminal isolates of interest using phyA (SEQ ID NO. 1) or portions thereof as probes by known techniques (Sambrook, 1989; Ausubel, 1990) as described in example 4B. Related nucleic acids may be cloned by employing known techniques. Radioisotopes (i.e., $^{32}$p) may be required when screening organisms with complex genomes in order to increase the sensitivity of the analysis. Polymerase chain reaction (PCR) amplification may also be used to identify genes related to phyA. Related sequences found in pure or mixed cultures are preferentially amplified by PCR (and variations of such as Reverse Transcription—PCR) with oligonucleotides primers designed using SEQ ID NO. 1. Amplified products may be visualized by agarose gel electrophoresis and cloned using known techniques. A variety of materials, including cells, colonies, plaques, and extracted nucleic acids (e.g., DNA, RNA), may be examined by these techniques for the presence of related sequences. Alternatively, known immunodetection techniques employing antibodies specific to PhyA (SEQ ID NO. 2) can be used to screen whole cells or extracted proteins of interest for the presence of related phytase(s).

TABLE 1

Phytase activity among rumen bacteria

| Phytase Activity | Microorganism | Number of isolates tested |
|---|---|---|
| Very Strong | Prevotella sp. | 1 |
|  | Selenomonas ruminantium | 11 |
| Strong | Prevotella ruminicola | 4 |
|  | S. ruminantium | 13 |
| Moderate | Bacillus sp. | 1 |
|  | Megasphaera elsdenii | 7 |
|  | P. ruminicola | 6 |
|  | S. ruminantium | 37 |
|  | Treponema sp. | 1 |
| Negative | Anaerovibrio lipolytica | 2 |
|  | Bacillus sp. | 4 |
|  | Butyrivibrio fibrisolvens | 47 |
|  | Clostridium sp. | 1 |
|  | Coprococcus sp. | 3 |
|  | Enterococcus sp. | 4 |
|  | Eubacterium sp. | 7 |
|  | Fibrobacter succinogenes | 8 |
|  | Fusobacterium sp. | 3 |
|  | Lachnospira multiparus | 4 |
|  | Lactobacillus sp. | 20 |
|  | M. elsdenii | 7 |
|  | Peptostreptococcus sp. | 1 |
|  | P. ruminicola | 41 |
|  | Ruminobacter amylophilus | 4 |
|  | Ruminococcus albus | 7 |
|  | Ruminococcus flavefaciens | 10 |
|  | S. ruminantium | 4 |
|  | Streptococcus bovis | 48 |
|  | Streptococcus milleri | 1 |
|  | Staphylococcus sp. | 6 |
|  | Succinovibrio dextrisolvens | 12 |
|  | Treponema sp. | 12 |
|  | Unknown | 8 |
|  | Total isolates screened | 345 |

TABLE 2

Phytase activity of selected rumen bacterial isolates

| Isolate | Phytase activity (mU*/mL) |
|---|---|
| Selenomonas ruminantium JY35 | 646 |
| Selenomonas ruminantium KJ118 | 485 |
| Selenomonas ruminantium BS131 | 460 |
| Selenomonas ruminantium HD141 | 361 |
| Selenomonas ruminantium HD86 | 286 |
| Selenomonas ruminantium JY135 | 215 |
| Selenomonas ruminantium D | 69 |
| Selenomonas ruminantium HD16 | 52 |
| Selenomonas ruminantium BS114 | 47 |
| Selenomonas ruminantium JY4 | 27 |
| Prevotella sp. 46/5[2] | 321 |
| Prevotella ruminicola JY97 | 68 |
| Prevotella ruminicola KJ182 | 61 |
| Prevotella ruminicola JY106 | 49 |
| Megasphaera elsdenii JY91 | 5 |

*U = $\mu$moles, $P_i$ released/min

TABLE 3

Overexpression of S. ruminantium[1] phytase in recombinant E.coli DH5α.

| Strain | Sample Composition | Units[2]/mL | Specific Activity (Units/mg protein) |
|---|---|---|---|
| E. coli (pSrP.2) | cells | 0.30 (0.08)[3] | 1.56 (0.41) |
|  | supernatant | 0.308 (0.21) | 2.64 (1.51) |
| E. coli (pSrPf6) | cells | 0.91 (0.41) | 6.42 (0.64) |
|  | supernatant | 5.10 (0.58) | 22.83 (1.67) |
| E coli (pSrP.2 Sphl) | cells | ND[4] | ND |
|  | supernatant | ND | ND |

[1]S. ruminantium JY35 is a gram-negative, obligately anaerobic, crescent-shaped rod. It produces propionic acid from fermentation of glucose, ferments lactose, and does not ferment glycerol or mannitol. [Bergey's Manual of Determinative Bacteriology, John G. Holt, ed., Williams and Wilkins, Baltimore MD, 1984.]
[2]Units = $\mu$moles $P_1$ released/min
[3]Numbers in parenthese are standard errors
[4]ND = not detected

TABLE 4

Growth and phytase activity of P. pastoris cells transformed with pPICZα:A (negative control) or pPICZα:A::MATE (clone 17).

| Culture | Time (h) | Optical Density (610 nm) | Phytase activity ($\mu$mol/min/mL) Culture | Supernatant |
|---|---|---|---|---|
| P. pastoris (pPICZαA) | 0.0 | 2.6 | 0.0 | 0.0 |
|  | 20.5 | 10.1 | 0.0 | 0.0 |
|  | 42.5 | 17.8 | 0.0 | 0.0 |
|  | 68.0 | 17.0 | 0.0 | 0.0 |
|  | 91.0 | 28.5 | 0.0 | 0.0 |
|  | 138.5 | 39.3 | 0.0 | 0.0 |
|  | 210.5 | 46.7 | 0.0 | 0.0 |
| P. pastoris (pPICZα:A::MATE) | 0.0 | 2.5 | 0.0 | 0.0 |
|  | 20.5 | 11.3 | 1.9 | 0.1 |
|  | 42.5 | 13.9 | 4.4 | 1.5 |
|  | 68.0 | 12.9 | 8.0 | 2.7 |
|  | 91.0 | 15.7 | 4.7 | 0.5 |
|  | 138.5 | 18.3 | 12.6 | 5.3 |
|  | 210.5 | 18.7 | 22.5 | 12.5 |

TABLE 5

The effect of Tween-80 concentration on growth and phytase activity of P. pastoris cells transformed with pPICZαA::MATE (clone 17).

| Time (d) | Sample (% Tween-80) | Optical Density (610 nm) | Phytase Activity ($\mu$mol/min/mL) Culture | Supernatant | Supernatant/ Culture Activity |
|---|---|---|---|---|---|
| 2 | 0.0 | 24.3 | 4.1 | 2.2 | 0.55 |
|  | 0.02 | 24.4 | 4.8 | 2.7 | 0.57 |
|  | 0.1 | 25.1 | 5.2 | 3.2 | 0.61 |
|  | 0.5 | 24.4 | 4.9 | 3.2 | 0.65 |
| 4 | 0.0 | 31.2 | 6.9 | 4.7 | 0.69 |
|  | 0.02 | 31.0 | 8.2 | 5.5 | 0.67 |
|  | 0.1 | 31.8 | 10.3 | 6.9 | 0.67 |
|  | 0.5 | 29.2 | 10.3 | 9.1 | 0.88 |
| 8 | 0.0 | 32.8 | 10.6 | 5.9 | 0.55 |
|  | 0.02 | 30.4 | 14.8 | 9.8 | 0.67 |
|  | 0.1 | 33.9 | 20.2 | 17.2 | 0.86 |
|  | 0.5 | 33.8 | 22.1 | 18.9 | 0.86 |

TABLE 6

The effect of incubation period and recombinant *S. ruminantium* JY35 phytase (2 units/g of corn) on phosphate release from corn.

| Sample | Length of incubation (h) | Phosphate concentration ($\mu$moles/mL) |
|---|---|---|
| No phytase | 1 | 0.85 |
| | 2 | 1.72 |
| | 3 | 2.56 |
| | 4 | 3.77 |
| | 5 | 4.35 |
| Phytase | 1 | 4.76 |
| | 2 | 6.83 |
| | 3 | 7.72 |
| | 4 | 8.41 |
| | 5 | 8.49 |

TABLE 7

The effect of recombinant *S. ruminantium* JY35 phytase concentration on phosphate release from corn.

| Phytase activity (units/g of corn) | Phosphate concentration ($\mu$moles/g of corn) |
|---|---|
| 0.08 | 11.8 |
| 0.16 | 14.8 |
| 0.24 | 22.5 |
| 0.32 | 23.0 |
| 0.40 | 23.2 |
| 0.48 | 23.8 |
| 0.56 | 23.8 |
| 0.64 | 23.6 |
| 0.72 | 23.8 |

REFERENCES

Al-Asheh, S. And Z. Duvnjak. 1994. The effect of surfactants on the phytase production and the reduction of the phytic content in canola meal by *Aspergillus carbonarius* during a solid state fermentation process. Biotechnol. Lett. 16:183–188.

Ausubel, F. A., R. Brent, R. E. Kingston, D. D. Moore, J. G. Sneidman, J. A. Smith and K. Struhl. (eds.) 1990. *Current protocols in molecular biology*. Green Publishing and Wiley-lnterscience, New York.

Brosius, J., M. Erfle and J. Storella. 1985. Spacing of the −10 and −35 regions in the tac promoter. J. Biol. Chem. 260:3539–3541.

Bryant, M. P. and L. A. Burkey. 1953. Cultural methods and some characteristics of some of the numerous groups of bacteria in the bovine rumen. J. Dairy Sci. 36:205–217.

Cheng, E. W., G. Hall and W. Burroughs. 1955. A method for the study of cellulose digestion by washed suspensions of rumen microorganisms. J. Dairy Sci. 38:1255–1230.

Cheng, K. -J. and J. W. Costerton, 1973. Localization of alkaline phosphatase in three Gram-negative rumen bacteria. J. Bacteriol. 116:424–440.

Dayhoff, M. O., R. M. Schwartz and B. C. Orcutt. 1978. A model of evoluntionary change in proteins. In: *Atlas of Protein Sequence and Structure*. Volume 5, Supplement 3, Chapter 22, pp 345–352.

Ellis, S. B., P. F. Brust, P. J. Koutz, A. F. Waters, M. M. Harpold and R. R. Gingeras. 1985. Isolation of alcohol oxidase and two other methanol regulated genes from the yeast, *Pichia pastoris*. Mol. Cell. Biol. 5:1111–1121.

Fiske, C. H. and Y. Subbarow. 1925. The colorimetric determination of phosphorus. J. Biol. Chem. 66:376–400.

Gelvin, S. B., R. A. Schilperoort and D. P. S. Verma (eds.). 1993. *Plant Molecular Biology Manual*. Kluwer Academic Publishers, Boston, Mass.

Graf, E. (ed.). 1986. *Phytic acid, chemistry and applications*. Pilatus Press. Minneapolis, Min. 344 pp.

Howson, S. J. and R. P. Davis. 1983. Production of phytate-hydrolysing enzyme by some fungi. Enzyme Microb. Technol. 5:377–382.

Hu, Y. J., D. C. Smith, K. -J. Cheng and C. W. Forsberg. 1991. Cloning of a xylanase gene from *Fibrobacter succinogenes* 135 and its expression in *Escherichia coli*. Can.J. Microbiol. 37:554–561.

Hungate, R. E. 1950. The anaerobic mesophilic cellulolytic bacteria. Bacteriol. Rev. 14:1–49.

Laemmli, U. K. 1970. Cleavage of the structural proteins during assembly of the head of bacteriophage T4. Nature 227:680–685.

Priefer, U., R. Simon and A. Puhler. 1984. Cloning with cosmids. In: Puhler, A. and K. N. Timmis (eds) *Advanced molecular genetics*. Springer-Verlag, New York. pp.190–201.

Raun, A., E. Cheng and W. Burroughs. 1956. Phytate phosphorus hydrolysis and availability to rumen microorganisms. Agric. Food Chem. 4:869–871.

Sambrook, J., E. F. Fritsch and T. Maniatis. 1989. *Molecular cloning. A laboratory manual*. 2nd. edn. Cold Spring Harbor Laboratory Press. Cold Spring Harbor, N.Y.

Scott, H. W. and B. A. Dehority. 1965. Vitamin requirements of several cellulolytic bacteria. J. Bacteriol. 89:1169–1175.

Shieh, T. R. and J. H. Ware. 1968. Survey of microorganisms for the production of extracellular phytase. Appl. Microbiol. 16:1348–1351.

van Gorcom, R. F. M. and C. A. M. J Van Den Hondel. 1993. Cloning, characterization and overexpression of the phytase gene (phyA) of *Aspergillus niger*. Gene 127:87–94.

van Hartingsveldt W., C. M. J. van Zeij, M. G. Harteveld, R. J. Gouka, M. E. G. Suykerbuyk, R. G. M. Luiten, P. A. Van Paridon, G. C. M. Selten, A. E. Veenstra, van Rooijen, G. J. H. and M. M. Moloney. 1994. Plant seed oil-bodies as carriers for foreign proteins. Bio/Technology 13:72–77.

von Heijne, G. 1986. A new method for predicting signal sequence cleavage sites. Nucleic Acids Res. 14:4683–4690.

Wong, S. -L. 1989. Development of an inducible and enhancible expression and secretion system in *Bacillus subtilis*. Gene 83:215–223.

All publications mentioned in this specification are indicative of the level of skill of those skilled in the art to which this invention pertains. All publications are herein incorporated by reference to the same extent as if each individual publication was specifically indicated to be incorporated by reference.

Although the foregoing invention has been described in some detail by way of illustration and example for purposes of clarity and understanding, it will be obvious that certain changes and modifications may be practised within the scope of the claims.

We claim:

1. A purified and isolated DNA encoding a phytase of a ruminal microorganism.

2. A purified and isolated DNA according to claim 1 wherein said ruminal microorganism is a prokaryote.

3. A purified and isolated DNA according to claim 1 wherein said ruminal microorganism is of the genus Selenomonas, Prevotella, Treponema or Megasphaera.

4. A purified and isolated DNA according to claim 1 wherein said ruminal microorganism is *Selenomonas ruminantium, Prevotella ruminicola, Treponema bryantii* or *Megasphaera elsdenii.*

5. A purified and isolated DNA according to claim 1 wherein said ruminal microorganism is *Selenomonas ruminantium.*

6. A purified and isolated DNA according to claim 5, wherein said encoded phytase has the following characteristics:

a) a molecular mass of about 37 kDa;

b) is active within a pH range of about 3.0 to 6.0; and c) is active within a temperature range of about 4 to 55° C.

7. A purified and isolated DNA according to claim 6 wherein said encoded phytase is active within a temperature range of about 20 to 55° C.

8. A purified and isolated DNA according to claim 6 wherein said encoded phytase is active within a temperature range of about 35 to 40° C.

9. A purified and isolated DNA according to claim 1 wherein said ruminal microorganism is *Selenomonas ruminantium* JY35 (ATCC 55785).

10. A purified and isolated DNA according to claim 1, said DNA being capable of hybridizing under stringent conditions with a probe comprising at least 25 continuous nucleotides of nucleotide sequence SEQ ID NO. 1 or the complement thereof.

11. A purified and isolated DNA according to claim 1, said phytase comprising amino acid sequence SEQ ID NO. 2.

12. A purified and isolated DNA according to claim 1, said DNA comprising nucleotide sequence SEQ ID NO. 1.

13. A purified and isolated DNA according to claim 1, said DNA comprising nucleotides 312–1268 of SEQ ID NO. 1.

14. A purified and isolated DNA according to any of claims 1, 2 or 3, wherein the encoded phytase has a specific activity at least two fold higher than that of *Aspergillus ficuum* NRRL 3135 PhyA:
wherein said specific activity is measured by an assay for the release of inorganic phosphate, said assay comprising the steps of:
a. mixing 150 μl of a buffered aqueous sample solution of a phytase for which the specific activity is to be tested with 600 μl of a phytate substrate solution comprising, 0.2% (w/v) sodium phytate in 0.1 M sodium acetate buffer to form a reaction mixture;
b. incubating said reaction mixture at pH 5.0 for 30 minutes at 37° C. whereby orthophosphate is released;
c. adding 750 μl of 5% (w/v) trichloroacetic acid to said reaction mixture, said colour reagent comprising 4 volumes of 1.5% (w/v ammonium molybdate in a sulfate solution, said colour reagent reacting with said released orthophosphate to produce phosphomolybdate;
d. measuring the amount of phosphomolybdate produced spectrophotometrically at a wavelength of 700 nm; and
e. determining the amount of inorganic phosphate released by comparing the amount of phosphomolybdate produced to a standard curve plotting the spectrophotometric measurements of samples of inorganic phosphate reacted with said colour reagent.

15. An expression construct capable of directing the expression of a phytase in a suitable host cell, said expression construct comprising a DNA encoding a phytase of a ruminal microorganism operably linked to control sequences compatible with said host cell.

16. An expression construct according to claim 15 wherein said ruminal microorganism is a prokaryote.

17. An expression construct according to claim 15 wherein said ruminal microorganism is of the genus Selenomonas, Prevotella, Treponema or Megasphaera.

18. An expression construct according to claim 15 wherein said ruminal microorganism is *Selenomonas ruminantium*.

19. An expression construct according to claim 18 wherein said encoded phytase has the following characteristics:

a) a molecular mass of about 37 kDa;
b) is active within a pH range of about 3.0 to 6.0; and
c) is active within a temperature range of about 4 to 55° C.

20. An expression construct according to claim 15 wherein said encoded phytase comprises amino acid sequence SEQ ID NO. 2.

21. An expression construct according to claim 20 wherein said DNA is capable of hybridizing under stringent conditions with a probe comprising at least 25 continuous nucleotides of nucleotide sequence SEQ ID NO. 1 or the complement thereof.

22. A host cell transformed with a DNA encoding a phytase of a ruminal microorganism so that the host cell can express the phytase encoded by said DNA.

23. A transformed host cell according to claim 22 wherein said ruminal microorganism is a prokaryote.

24. A transformed host cell according to claim 22 wherein said ruminal microorganism is of the genus Selenomonas, Prevotella, Treponema or Megasphaera.

25. A transformed host cell according to claim 22 wherein said ruminal microorganism is *Selenomonas ruminantium*.

26. A transformed host cell according to claim 25 wherein said encoded phytase has the following characteristics:
a) a molecular mass of about 37 kDa;
b) is active within a pH range of about 3.0 to 6.0; and
c) is active within a temperature range of about 4 to 55° C.

27. A transformed host cell according to claim 22 wherein said encoded phytase comprises amino acid sequence SEQ ID NO. 2.

28. A transformed host cell according to claim 22 wherein said DNA is capable of hybridizing under stringent conditions with a probe comprising at least 25 continuous nucleotides of nucleotide sequence SEQ ID NO. 1 or the complement thereof.

29. A transformed host cell according to claim 22 wherein said host cell is a eukaryote.

30. A transformed host cell according to claim 22 wherein said host cell is a prokaryote.

31. A transformed host cell according to claim 22 wherein said host cell is a *Pichea pastoris* cell.

32. A transformed host cell according to claim 22 wherein said host cell is a *Bacillus subtilis* cell.

33. A transformed host cell according to claim 22 wherein said host cell is an *E. coli* cell.

34. A transgenic plant transformed with a DNA encoding a phytase of a ruminal microorganism so that the phytase encoded by said DNA can be expressed by said plant.

35. A transgenic plant according to claim 34 wherein said ruminal microorganism is a prokaryote.

36. A transgenic plant according to claim 34 wherein said ruminal microorganism is of the genus Selenomonas, Prevotella, Treponerna or Megasphaera.

37. A transgenic plant according to claim 34 wherein said ruminal microorganism is *Selenomonas ruminantium*.

38. A transgenic plant according to claim 37 wherein said encoded phytase has the following characteristics:
a) a molecular mass of about 37 kDa;
b) is active within a pH range of about 3.0 to 6.0; and
c) is active within a temperature range of about 4 to 55° C.

39. A transgenic plant according to claim 27 wherein said encoded phytase comprises amino acid sequence SEQ ID NO. 2.

40. A transgenic plant according to claim 34 wherein said DNA is capable of hybridizing under stringent conditions with a probe comprising at least 25 continuous nucleotides of nucleotide sequence SEQ ID NO. 1 or the complement thereof.

41. A transgenic plant according to any one of claims 34, 35, 36, 37, 38, 39, or 40 wherein said plant is of the species *Brassica napus*.

42. A method for producing a phytase, comprising:
 (a) transforming at least one host cell with a DNA encoding a phytase of a ruminal microorganism so that said host cell can express said phytase; and
 (b) growing a culture of said host cells under conditions conducive to the expression of said phytase by said host cells.

43. A method according to claim 42 comprising the further step of:
 (c) extracting said phytase from said culture.

44. A method according to claim 42 wherein said ruminal microorganism is a prokaryote.

45. A method according to claim 42 wherein said ruminal microorganism is of the genus Selenomonas, Prevotella, Treponema or Megasphaera.

46. A method according to claim 42 wherein said ruminal microorganism is *Selenomonas ruminantium*.

47. A method according to claim 46 wherein said encoded phytase has the following characteristics:
 a) a molecular mass of about 37 kDa;
 b) is active within a pit range of about 3.0 to 6.0; and
 c) is active within a temperature range of about 4 to 55° C.

48. A method according to claim 42 wherein said phytase comprises amino acid sequence SEQ ID NO. 2.

49. A method according to claim 42 wherein said DNA is capable of hybridizing under stringent conditions with a probe comprising at least 25 continuous nucleotides of nucleotide sequence SEQ ID NO. 1 or the complement thereof.

50. A method for producing a transgenic plant, comprising:
 (a) transforming a plant with a DNA encoding a phytase of a ruminal microorganism so that said plant can express said phytase; and
 (b) growing said plant under conditions conducive to the expression of said phytase by said plant.

51. A method according to claim 50 wherein said ruminal microorganism is a prokaryote.

52. A method according to claim 50 wherein said ruminal microorganism is of the genus Selenomonas, Prevotella, Treponema or Megasphaera.

53. A method according to claim 50 wherein said ruminal microorganism is *Selenomonas ruminantium*.

54. A method according to claim 53 wherein said encoded phytase has the following characteristics:
 a) a molecular mass of about 37 kDa;
 b) is active within a pH range of about 3.0 to 6.0, and
 c) is active within a temperature range of about 4 to 55° C.

55. A method according to claim 50 wherein said phytase comprises amino acid sequence SEQ ID NO. 2.

56. A method according to claim 50 wherein said DNA is capable of hybridizing under stringent conditions with a probe comprising at least 25 continuous nucleotides of nucleotide sequence SEQ ID NO. 1 or the complement thereof.

57. A method according to any one of claims 50, 51, 52, 53, 54, 55, or 56 wherein said plant is of the species *Brassica napus*.

58. A purified and isolated DNA according to claim 1, wherein said encoded phytase comprises the amino acid sequence of SEQ ID NO.2 from amino acid number 10 to amino acid number 319.

59. A purified and isolated DNA according to claim 1, wherein said encoded phytase comprises the amino acid sequence of SEQ ID NO.2 from amino acid number 31 to amino acid number 319.

* * * * *

UNITED STATES PATENT AND TRADEMARK OFFICE
CERTIFICATE OF CORRECTION

PATENT NO. : 5,985,605

DATED : November 16, 1999

INVENTOR(S) : Cheng et al.

It is certified that error appears in the above-identified patent and that said Letters Patent is hereby corrected as shown below:

At column 40, line 63, claim 39, please rewrite "27" as --34--.

Signed and Sealed this

Seventh Day of November, 2000

Attest:

Q. TODD DICKINSON

*Attesting Officer*          *Director of Patents and Trademarks*

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 1401 base pairs
       (B) TYPE: nucleic acid
       (C) STRANDEDNESS: double
       (D) TOPOLOGY: circular (ii) MOLECULE TYPE: DNA (genomic)

(iii) HYPOTHETICAL: NO (iv) ANTI-SENSE: NO (vi) ORIGINAL SOURCE:
       (A) ORGANISM: Selenomonas ruminantium
       (B) STRAIN: JY35

(vii) IMMEDIATE SOURCE:
       (A) LIBRARY: Genomic DNA library
       (B) CLONE: pSrP.2

(ix) FEATURE:
       (A) NAME/KEY: CDS
       (B) LOCATION: 231..1268
       (C) IDENTIFICATION METHOD: experimental
       (D) OTHER INFORMATION: /codon_start= 231
          /function= "Dephosphorylation of phytic acid"
          /product= "Phytase"
          /evidence= EXPERIMENTAL
          /gene= "phyA"
          /number= 1
          /standard_name= "myo-inositol hexaphosphate
          phosphohydrolase"
          /citation= ([1])

(ix) FEATURE:
       (A) NAME/KEY: sig_peptide
       (B) LOCATION: 231..311
       (C) IDENTIFICATION METHOD: experimental
       (D) OTHER INFORMATION: /codon_start= 1
          /function= "phytase secretion"
          /product= "Signal peptide"
          /evidence= EXPERIMENTAL
          /citation= ([1])

(ix) FEATURE:
       (A) NAME/KEY: mat_peptide
       (B) LOCATION: 312..1268
       (C) IDENTIFICATION METHOD: experimental
       (D) OTHER INFORMATION: /codon_start= 312
          /product= "Phytase"
          /evidence= EXPERIMENTAL
          /number= 2
          /citation= ([1])

(xi) SEQUENCE DESCRIPTION: SEQ ID NO:1:

```
CGTCCACGGA GTCACCCTAC TATACGACGT ATGTGAAGTT CACGTCGAAG TTCTAGGGAA      60

TCACCGATTC GTGCAGGATT TTACCACTTC CTGTTGAAGC GGATGAGAAG GGGAACCGCG     120

AAGCGGTGGA AGAGGTGCTG CACGACGGAC GATCGCGCTG AATGAATCAG TGCTTCCTAA     180

CTATTGGGAT TCCGCGCAGA CGCGCGGATG GAGTAAAGGA GTAAGTTGTT ATG AAA        236
                                                     Met Lys
                                                     -27

TAC TGG CAG AAG CAT GCC GTT CTT TGT AGT CTC TTG GTC GGC GCA TCC       284
Tyr Trp Gln Lys His Ala Val Leu Cys Ser Leu Leu Val Gly Ala Ser
-25                 -20                 -15                 -10
```

```
CTC TGG ATA CTG CCG CAG GCC GAT GCG GCC AAG GCG CCG GAG CAG ACG      332
Leu Trp Ile Leu Pro Gln Ala Asp Ala Ala Lys Ala Pro Glu Gln Thr
            -5                   1               5

GTG ACG GAG CCC GTT GGG AGC TAC GCG CGC GCG GAG CGG CCG CAG GAC      380
Val Thr Glu Pro Val Gly Ser Tyr Ala Arg Ala Glu Arg Pro Gln Asp
        10                  15                  20

TTC GAG GGC TTT GTC TGG CGC CTC GAC AAC GAC GGC AAG GAG GCG TTG      428
Phe Glu Gly Phe Val Trp Arg Leu Asp Asn Asp Gly Lys Glu Ala Leu
    25                  30                  35

CCG CGT AAT TTC CGC ACG TCG GCT GAC GCG CTG CGC GCG CCG GAG AAG      476
Pro Arg Asn Phe Arg Thr Ser Ala Asp Ala Leu Arg Ala Pro Glu Lys
40              45                  50                  55

AAA TTC CAT CTC GAC GCC GCG TAT GTA CCG TCG CGC GAG GGC ATG GAT      524
Lys Phe His Leu Asp Ala Ala Tyr Val Pro Ser Arg Glu Gly Met Asp
                60                  65                  70

GCA CTC CAT ATC TCG GGC AGT TCC GCA TTC ACG CCG GCG CAG CTC AAG      572
Ala Leu His Ile Ser Gly Ser Ser Ala Phe Thr Pro Ala Gln Leu Lys
                75                  80                  85

AAC GTT GCC GCG AAG CTG CGG GAG AAG ACG GCT GGC CCC ATC TAC GAT      620
Asn Val Ala Ala Lys Leu Arg Glu Lys Thr Ala Gly Pro Ile Tyr Asp
            90                  95                 100

GTC GAC CTA CGG CAG GAG TCG CAC GGC TAT CTC GAC GGT ATC CCC GTG      668
Val Asp Leu Arg Gln Glu Ser His Gly Tyr Leu Asp Gly Ile Pro Val
        105                 110                 115

AGC TGG TAC GGC GAG CGC GAC TGG GCA AAT CTC GGC AAG AGC CAG CAT      716
Ser Trp Tyr Gly Glu Arg Asp Trp Ala Asn Leu Gly Lys Ser Gln His
120                 125                 130                 135

GAG GCG CTC GCC GAC GAG CGG CAC CGC TTG CAC GCA GCG CTC CAT AAG      764
Glu Ala Leu Ala Asp Glu Arg His Arg Leu His Ala Ala Leu His Lys
                140                 145                 150

ACG GTC TAC ATC GCG CCG CTC GGC AAG CAC AAG CTC CCC GAG GGC GGC      812
Thr Val Tyr Ile Ala Pro Leu Gly Lys His Lys Leu Pro Glu Gly Gly
            155                 160                 165

GAA GTC CGC CGC GTA CAG AAG GTG CAG ACG GAA CAG GAA GTC GCC GAG      860
Glu Val Arg Arg Val Gln Lys Val Gln Thr Glu Gln Glu Val Ala Glu
        170                 175                 180

GCC GCG GGG ATG CGC TAT TTC CGC ATC GCG GCG ACG GAT CAT GTC TGG      908
Ala Ala Gly Met Arg Tyr Phe Arg Ile Ala Ala Thr Asp His Val Trp
185                 190                 195

CCA ACG CCG GAG AAC ATC GAC CGC TTC CTC GCG TTT TAC CGC ACG CTG      956
Pro Thr Pro Glu Asn Ile Asp Arg Phe Leu Ala Phe Tyr Arg Thr Leu
200                 205                 210                 215

CCG CAG GAT GCG TGG CTC CAT TTC CAT TGT GAA GCC GGT GTC GGC CGC     1004
Pro Gln Asp Ala Trp Leu His Phe His Cys Glu Ala Gly Val Gly Arg
                220                 225                 230

ACG ACG GCG TTC ATG GTC ATG ACG GAT ATG CTG AAG AAC CCG TCC GTA     1052
Thr Thr Ala Phe Met Val Met Thr Asp Met Leu Lys Asn Pro Ser Val
            235                 240                 245

TCG CTC AAG GAC ATC CTC TAT CGC CAG CAC GAG ATC GGC GGC TTT TAC     1100
Ser Leu Lys Asp Ile Leu Tyr Arg Gln His Glu Ile Gly Gly Phe Tyr
        250                 255                 260

TAC GGG GAG TTC CCC ATC AAG ACG AAG GAT AAA GAT AGC TGG AAG ACG     1148
Tyr Gly Glu Phe Pro Ile Lys Thr Lys Asp Lys Asp Ser Trp Lys Thr
265                 270                 275

AAA TAT TAT AGG GAA AAG ATC GTG ATG ATC GAG CAG TTC TAC CGC TAT     1196
Lys Tyr Tyr Arg Glu Lys Ile Val Met Ile Glu Gln Phe Tyr Arg Tyr
280                 285                 290                 295

GTG CAG GAG AAC CGC GCG GAT GGC TAC CAG ACG CCG TGG TCG GTC TGG     1244
Val Gln Glu Asn Arg Ala Asp Gly Tyr Gln Thr Pro Trp Ser Val Trp
                300                 305                 310
```

```
CTC AAG AGC CAT CCG GCG AAG GCG TAAAAGCGCA GGCGGCGGCT CGGAGTCAGG    1298
Leu Lys Ser His Pro Ala Lys Ala
            315

GAAATGGCGC TGCCAGCACG GGACGCGCGG CGGCGGATGC TGCGCCGGTC AGGGATGATT    1358

GACGACAGCC AGAGAAGAAA GGATGGTTTT ATGAGGTGGA TCC                      1401
```

(2) INFORMATION FOR SEQ ID NO:2:

(i) SEQUENCE CHARACTERISTICS:
        (A) LENGTH: 346 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Tyr Trp Gln Lys His Ala Val Leu Cys Ser Leu Leu Val Gly
-27     -25                 -20                 -15

Ala Ser Leu Trp Ile Leu Pro Gln Ala Asp Ala Ala Lys Ala Pro Glu
    -10                  -5                   1                   5

Gln Thr Val Thr Glu Pro Val Gly Ser Tyr Ala Arg Ala Glu Arg Pro
                10                  15                  20

Gln Asp Phe Glu Gly Phe Val Trp Arg Leu Asp Asn Asp Gly Lys Glu
            25                  30                  35

Ala Leu Pro Arg Asn Phe Arg Thr Ser Ala Asp Ala Leu Arg Ala Pro
        40                  45                  50

Glu Lys Lys Phe His Leu Asp Ala Tyr Val Pro Ser Arg Glu Gly
    55                  60                  65

Met Asp Ala Leu His Ile Ser Gly Ser Ser Ala Phe Thr Pro Ala Gln
70                  75                  80                  85

Leu Lys Asn Val Ala Ala Lys Leu Arg Glu Lys Thr Ala Gly Pro Ile
                90                  95                  100

Tyr Asp Val Asp Leu Arg Gln Glu Ser His Gly Tyr Leu Asp Gly Ile
                105                 110                 115

Pro Val Ser Trp Tyr Gly Glu Arg Asp Trp Ala Asn Leu Gly Lys Ser
            120                 125                 130

Gln His Glu Ala Leu Ala Asp Glu Arg His Arg Leu His Ala Ala Leu
    135                 140                 145

His Lys Thr Val Tyr Ile Ala Pro Leu Gly Lys His Lys Leu Pro Glu
150                 155                 160                 165

Gly Gly Glu Val Arg Arg Val Gln Lys Val Gln Thr Glu Gln Glu Val
                170                 175                 180

Ala Glu Ala Ala Gly Met Arg Tyr Phe Arg Ile Ala Ala Thr Asp His
            185                 190                 195

Val Trp Pro Thr Pro Glu Asn Ile Asp Arg Phe Leu Ala Phe Tyr Arg
        200                 205                 210

Thr Leu Pro Gln Asp Ala Trp Leu His Phe His Cys Glu Ala Gly Val
    215                 220                 225

Gly Arg Thr Thr Ala Phe Met Val Met Thr Asp Met Leu Lys Asn Pro
230                 235                 240                 245

Ser Val Ser Leu Lys Asp Ile Leu Tyr Arg Gln His Glu Ile Gly Gly
                250                 255                 260

Phe Tyr Tyr Gly Glu Phe Pro Ile Lys Thr Lys Asp Lys Asp Ser Trp
            265                 270                 275

Lys Thr Lys Tyr Tyr Arg Glu Lys Ile Val Met Ile Glu Gln Phe Tyr
        280                 285                 290
```

```
Arg Tyr Val Gln Glu Asn Arg Ala Asp Gly Tyr Gln Thr Pro Trp Ser
    295                 300                 305

Val Trp Leu Lys Ser His Pro Ala Lys Ala
310                 315
```

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide SrPr6"

(iii) HYPOTHETICAL: NO (iv) ANTI-SENSE: NO (vi) ORIGINAL SOURCE:
        (A) ORGANISM: Selenomonas ruminantium
        (B) STRAIN: JY35

(vii) IMMEDIATE SOURCE:
        (A) LIBRARY: Genomic DNA library
        (B) CLONE: pSrP.2

(xi) SEQUENCE DESCRIPTION: SEQ ID NO:3:

CGGGATGCTT CTGCCAGTAT        20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide SrPf6"

(iii) HYPOTHETICAL: NO (iv) ANTI-SENSE: NO (vi) ORIGINAL SOURCE:
        (A) ORGANISM: Selenomonas ruminantium
        (B) STRAIN: JY35

(vii) IMMEDIATE SOURCE:
        (A) LIBRARY: Genomic DNA library
        (B) CLONE: pSrP.2

(xi) SEQUENCE DESCRIPTION: SEQ ID NO:4:

CGTCCACGGA GTCACCCTAC        20

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide MATE2"

(iii) HYPOTHETICAL: NO (iv) ANTI-SENSE: NO (vi) ORIGINAL SOURCE:
        (A) ORGANISM: Selenomonas ruminantium (B) STRAIN: JY35

(vii) IMMEDIATE SOURCE:
          (A) LIBRARY: Genomic DNA library
          (B) CLONE: pSrP.2

(xi) SEQUENCE DESCRIPTION: SEQ ID NO:5:

GCGAATTCAT GGCCAAGGCG CCGGAGCAGA C                                          31

(2) INFORMATION FOR SEQ ID NO:6:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide MATE"

(iii) HYPOTHETICAL: NO (iv) ANTI-SENSE: NO (vi) ORIGINAL SOURCE:
          (A) ORGANISM: Selenomonas ruminantium
          (B) STRAIN: JY35

(vii) IMMEDIATE SOURCE:
          (A) LIBRARY: Genomic DNA library
          (B) CLONE: pSrP.2

(xi) SEQUENCE DESCRIPTION: SEQ ID NO:6:

GCGAATTCGC CAAGGCGCCG GAGCAGAC                                              28

(2) INFORMATION FOR SEQ ID NO:7:

(i) SEQUENCE CHARACTERISTICS:
          (A) LENGTH: 31 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide MATN"

(iii) HYPOTHETICAL: NO (iv) ANTI-SENSE: NO (vi) ORIGINAL SOURCE:
          (A) ORGANISM: Selenomonas ruminantium
          (B) STRAIN: JY35

(vii) IMMEDIATE SOURCE:
          (A) LIBRARY: Genomic DNA library
          (B) CLONE: pSrP.2

(xi) SEQUENCE DESCRIPTION: SEQ ID NO:7:

GAGGATCCAT GGCCAAGGCG CCGGAGCAGA C                                          31